United States Patent [19]
Minshall et al.

[11] Patent Number: 5,672,481
[45] Date of Patent: Sep. 30, 1997

[54] APPARATUS AND METHOD FOR PARTICLE SEPARATION IN A CLOSED FIELD

[75] Inventors: Billy W. Minshall, Mill Creek; Patrick M. Maloney; Fred Mill, both of Bothell; Shelly Heimfeld, Woodinville; Stanley Corpuz, Kirkland; Penny Thompson, Snohomish; Eric Peterson, Seattle, all of Wash.

[73] Assignee: Cellpro, Incorporated, Bothell, Wash.

[21] Appl. No.: 52,784

[22] Filed: Apr. 23, 1993

Related U.S. Application Data

[63] Continuation-in-part of Ser. No. 5,891, Jan. 15, 1993, abandoned, which is a continuation of Ser. No. 780,750, Oct. 23, 1991, Pat. No. 5,240,856.

[51] Int. Cl.⁶ .................... G01N 33/49; G01N 33/543
[52] U.S. Cl. .................. 435/7.21; 435/2; 435/287; 435/311; 435/316; 436/518; 436/176; 436/177; 436/178; 422/44; 422/59
[58] Field of Search .................. 435/7.21, 2, 299, 435/311, 961, 962, 287, 316; 436/518, 541, 176, 177, 178; 422/44, 59, 68.1; 210/782, 800, 103; 604/405, 406, 409, 410, 416

[56] References Cited

U.S. PATENT DOCUMENTS

| Re. 33,924 | 5/1992 | Valeri . | |
|---|---|---|---|
| 3,115,460 | 12/1963 | McCormick . | |
| 3,299,693 | 1/1967 | Kieselbach | 73/23.1 |
| 3,347,454 | 10/1967 | Bellamy, Jr. et al. . | |
| 3,645,687 | 2/1972 | Nerenberg | 23/230 R |
| 3,679,128 | 7/1972 | Unger et al. . | |
| 3,987,961 | 10/1976 | Sinn et al. . | |
| 4,004,975 | 1/1977 | Lionetti | 195/1.8 |
| 4,098,456 | 7/1978 | Bayham . | |
| 4,111,199 | 9/1978 | Djerassi . | |
| 4,146,172 | 3/1979 | Cullis et al. . | |
| 4,162,855 | 7/1979 | Bender . | |
| 4,223,672 | 9/1980 | Terman et al. | 604/5 |
| 4,285,464 | 8/1981 | Latham, Jr. . | |
| 4,316,576 | 2/1982 | Cullis et al. . | |
| 4,413,772 | 11/1983 | Rohde et al. . | |

(List continued on next page.)

FOREIGN PATENT DOCUMENTS

| 0288425 | 10/1988 | European Pat. Off. . |
|---|---|---|
| 2647213 | 11/1990 | France . |
| WO90/04784 | 3/1990 | WIPO . |

OTHER PUBLICATIONS

Pertoft, H. et al "Sedimentation of Cells in Colloidal Silica (Percoll)," pp. 115–152 in *Cell Separation*, Pretlow eds. 1982 vol. 1.

Spectrum®, "Dialysis/Ultrafiltration," pp. 8–11, 66–73, 94, 98–99.

"MicroKros™ Syringe Filters Crossflow Microporous Separations from 1 ml to 20 ml," Microgon, Inc., (no date).

*Primary Examiner*—James C. Housel
*Assistant Examiner*—Rachel Heather Freed
*Attorney, Agent, or Firm*—Townsend and Townsend and Crew LLP

[57] ABSTRACT

A particle separator is provided for collection and manipulation of target particles, e.g., target cells, in a closed sterile field condition. In one embodiment, closed sterile field conditions are maintained from separation through concentration and/or cryo treatment steps and/or transfusion. Preservation of closed sterile field condition are accommodated by using the same integrally coupled rigid-walled vessel for collection and concentration and transfer via integrally coupled conduits to a vessel for cryopreservation and/or transfusion.

In one embodiment, a plurality of valves are responsive to a data processor for controlling the path of fluid flow through the particle separator. A plurality of sensors are provided for providing sensor signals indicative of fluid flowing through the cell separator. A peristaltic pump is responsive to the microprocessor assembly for controlling the speed and direction of fluid flow through the system. A stir plate assembly is responsive to a signal from the data processor for controllably agitating the contents of the cell separator.

24 Claims, 15 Drawing Sheets

U.S. PATENT DOCUMENTS

| | | | |
|---|---|---|---|
| 4,439,177 | 3/1984 | Conway . | |
| 4,482,342 | 11/1984 | Lueptow et al. . | |
| 4,512,763 | 4/1985 | Schneider | 604/5 |
| 4,531,932 | 7/1985 | Luppi et al. . | |
| 4,610,846 | 9/1986 | Martin . | |
| 4,619,639 | 10/1986 | Nose et al. | 604/8 |
| 4,675,286 | 6/1987 | Calenoff | 435/7 |
| 4,714,457 | 12/1987 | Alterbaum . | |
| 4,720,284 | 1/1988 | McCarty . | |
| 4,734,372 | 3/1988 | Rotman | 435/291 |
| 4,755,357 | 7/1988 | Robbins et al. . | |
| 4,761,366 | 8/1988 | Nakajima et al. | 435/2 |
| 4,807,676 | 2/1989 | Cerny et al. . | |
| 4,810,378 | 3/1989 | Carmen et al. . | |
| 4,820,297 | 4/1989 | Kaufman et al. . | |
| 4,834,890 | 5/1989 | Brown et al. . | |
| 4,840,730 | 6/1989 | Sexena | 210/198.2 |
| 4,880,425 | 11/1989 | Kuhlemann et al. . | |
| 4,892,668 | 1/1990 | Harmony et al. . | |
| 4,909,949 | 3/1990 | Harmony et al. . | |
| 4,915,847 | 4/1990 | Dillon et al. . | |
| 4,917,804 | 4/1990 | Franks et al. . | |
| 4,994,021 | 2/1991 | Smith et al. . | |
| 4,994,056 | 2/1991 | Ikeda . | |
| 5,009,654 | 4/1991 | Minshall | 604/410 |
| 5,098,842 | 3/1992 | Nakajima et al. | 435/287 |
| 5,100,564 | 3/1992 | Pall et al. . | |
| 5,114,004 | 5/1992 | Isono et al. . | |
| 5,180,504 | 1/1993 | Johnson et al. . | |
| 5,181,910 | 1/1993 | Scanlon . | |
| 5,211,626 | 5/1993 | Frank et al. . | |
| 5,224,921 | 7/1993 | Dennehey et al. . | |
| 5,240,856 | 8/1993 | Goffe | 435/299 |
| 5,254,314 | 10/1993 | Yu et al. . | |
| 5,262,070 | 11/1993 | Ishida . | |
| 5,295,964 | 3/1994 | Gauthier . | |
| 5,314,421 | 5/1994 | Leuenberger . | |
| 5,336,760 | 8/1994 | Hardwick . | |

APPARATUS AND METHOD FOR PARTICLE SEPARATION IN A CLOSED FIELD

This application is a continuation-in-part of application Ser. No. 08/005,891 filed Jan. 15, 1993, abandoned, which is a continuation of U.S. Ser. No. 07/780,750, filed Oct. 23, 1991, for "Improved Apparatus and Method for Cell Separation" both of which are incorporated herein by reference, now U.S. Pat. No. 5,240,856.

The present invention is directed in general toward methods and apparatus for selecting target particles such as specific target cells from a heterogeneous population thereof in a sample fluid and, more particularly, toward improved apparatus for controlling the operation of a device for performing immunoselection of target cells, preferably in a closed field.

BACKGROUND OF THE INVENTION

Various methods and devices exist for separating component parts of a sample fluid to obtain target particles such as cells. These methods include filters, centrifuges, chromatographs, and other well-known fluid separation methods. Other apparatus and methods exist for separating a particular cell subpopulation, or target cells, from a mixture of cells. These methods include gross separation using columns, centrifuges, filters, separation by killing of unwanted cells, separation with fluorescence activated cell sorters, separation by directly or indirectly binding cells to a ligand immobilized on a physical support, such as panning techniques, separation by column immunoadsorption, and separation using magnetic immunobeads. Such immunoselection methods have been used to either positively or negatively select target cells, wherein positive selection refers to the direct selection and recovery of specific target cells, while negative selection refers to the elimination of a specific target cell subpopulation from a heterogeneous population of cells.

Columns are common to the above described methods for general separation of target particles, such as target cells from a mixture of cells in a sample fluid, and for the more specific immunoselection methods for selecting target cells from a sample fluid. Typically, a column has an entrance end, an exit end, and a substrate positioned intermediate the entrance and exit ends. In operation, the sample fluid is provided to the entrance end of the column and is moved through the column under pressure. As the sample fluid passes through the column, the substrate binds a subpopulation of cells from among the mixture of cells in the sample fluid so that the fluid exiting the column is fractionated with respect to the cell mixture. In one embodiment, the substrate separates the target particle from the fluid composition so that the target particle exiting the column will be substantially pure. The target cells flowing through the column can be collected and retained as the product of the separation. Alternatively, the flow-through can be discarded and the cells which are bound to the substrate can be eluted and collected. Accordingly, the substrate is chosen for a particular separation to separate the target particle (e.g., cells) from other particles contained in the sample fluid by a negative or a positive selection process.

In many situations, it is preferred to avoid loss of target particles, such as cells. In some devices, the conduits or other flow paths along which the target cells travel contain relatively sharp (low radius of curvature) turns, or angled turns such as right angle turns. These configurations can lead to undesirable particle or cell loss. Without wishing to be bound by any theory, it is believed that part or all of such loss may involve fluid dynamic factors such as the creation of small eddies or "dead" spaces having little or no net particle mass transport along the conduit, thus resulting in some or all of the particles or cells being retained in the conduit and not being transported to the target particle collection vessel. In previous devices, it has been particularly difficult to design conduits in the region of a agitator such as a magnetic stirrer which are not subject to this type of cell loss to an undesirable degree.

Various substrates exist for use with columns to separate the target particle from the sample fluid. Generally, the type of substrate chosen for performing the separation will determine how the target particles are separated from the sample fluid. As an example, in high-performance liquid chromatography (HPLC), the sample fluid is forced through the column under pressure using a solvent solution. The substrate is chosen so that the target particles exhibit substantially different binding characteristics with the substrate than the remaining components of the sample fluid so that the time necessary for the target particles to pass through the substrate will be substantially different from the time necessary for the remaining components of the sample fluid to pass through the substrate. Accordingly, a substantially pure composition of the target particles will exit the column at a predetermined time for collection.

In reference to immunoselection methods utilizing immunoadsorption devices, a ligand, such as an antibody, may be immobilized on the substrate. For example, using a separation device such as a column immunoabsorption device, the substrate may contain beads that have been coated with a ligand, immobilized on the surface of the beads. The ligand is chosen to specifically bind the target particles, thereby immobilizing the target particles within the separation device. After an adequate amount of the fluid composition has been passed through the separation device, to remove unbound cells from the device and/or to saturate the substrate, the target particles can be liberated from the substrate using various techniques. In one embodiment, the target particles are liberated from the substrate (such as beads) by gently agitating the substrate to break the bond between the target particles and the immobilized ligand.

Previous devices and methods have provided a degree of particle separation in a fashion which is not entirely contained in a closed field. In this context, closed field refers to a process and apparatus in which there is no exposure of the target particles to the environment between the time the sample containing the target particles is provided at the beginning of the method or apparatus and at least the time at which the target particles have been substantially separated. Previous devices and methods have also provided a degree of particle separation which is not entirely a sterile field. In one embodiment, the present invention provides particle separation in a closed field and, preferably, a sterile field. In one embodiment, the present invention provides a sterile field having fewer than a predetermined number of live cells per cubic centimeter. In one embodiment, closed field conditions, preferably sterile field conditions, are maintained beyond the time of particle separation, such as until particle concentration (such as by centrifugation or other means) cryopreservation, and/or reconstruction for infusion can involve, for example, addition of cryo media and/or cooling to cryogenic temperatures such as about $-20°$ to $-196°$ centigrade, as well as the resuspension of cells for transfusion after cryopreservation.

It is recognized that no procedure can provide a perfectly closed field or a perfectly sterile field in the sense that it is impossible to absolutely eliminate all exposure to the environment, such as exposure to all ambient molecules or radiation. In this context, closed field will be understood to mean substantially closed field, i.e., with sufficient protection from exposure to the environment to prevent the introduction or proliferation of microorganisms. For example, when the particles being separated are human stem cells for use in medical treatment, the apparatus and procedure should provide sufficient closed field characteristics that the separated stem cells are protected from exposure to potentially harmful aspects of the environment such as bacteria, viruses and other microorganisms. In this example, exposure to ambient atmosphere via an appropriate filter, such as for eliminating contaminants with a size greater than about 0.22 microns, is substantially a closed field.

Certain previous methods and devices have involved time-consuming or relatively expensive procedures. For example, certain devices require relatively complicated preparation or manipulation, such as involved insertion of tubing or other conduits, e.g., for the purpose of fluid transfer, or the requirement for preparing certain portions of the apparatus prior to introduction of the sample fluid, such as a protein loading requirement. Certain previous devices have included reusable apparatus which can come in contact with the target particles, thus either, requiring careful and extensive sterilization and/or risking contamination.

In view of these items, it is desirable to provide a fluid separation apparatus which results in a substantially closed, preferably sterile, field procedure for isolating target particles, at least through the separation stage and in some embodiments, through concentration and/or cryopreservation. It is desirable to provide an apparatus and method which is simpler, less error-prone and less time-consuming than previous devices and methods and having a reduced risk of contamination.

Some devices for performing immunoadsorption have proven undesirable since they have failed to provide commercially acceptable apparatus for agitating the substrate to aid in liberating the target particles. Some devices have also failed to provide apparatus for controlling the amount of agitation provided to the substrate, to prevent damage to the target particles and are further undesirable for this reason.

Separation devices, and particularly immunoadsorption devices, have also proven inefficient since these devices require considerable intervention from the operator to control the introduction of the sample fluid to the column as well as controlling the withdrawal of the target particle, such as cells, from the column. Typically, separation devices must be actively monitored through various stages including stages for cleansing the separation device prior to introduction of the sample fluid and for passing the sample fluid through the separation device. These stages generally require significant intervention from the operator to perform each of the foregoing steps of the fluid separation process, and to perform substeps within these steps. Accordingly, the efficiency of these devices is necessarily limited by the skill and effectiveness of the operator controlling the process.

It is further desirable, therefore, to provide apparatus for performing fluid separation that minimizes the amount of intervention necessary from an operator of the apparatus. Additionally, it is desirable to provide apparatus for performing fluid separation wherein the movement of fluid through the apparatus may be precisely controlled by the separation apparatus without significant intervention by the operator.

SUMMARY OF THE INVENTION

The subject invention provides improved apparatus and method for separating target particles from a sample fluid. In one embodiment of the present invention, an improved fluid control system is provided for use with a cell separation device assembly. In one embodiment, the separation device is a column separation assembly. Other types of separation devices are also possible, including filters, single or multiple plates such as immunoabsorption plates (so-called "condo plates") and magnetic beads. In the embodiment depicted in FIG. 10, the cell separation device assembly includes a column 1002 (FIG. 10) for separating target cells from a sample fluid 1004. The cell separation device assembly also includes a fluid collection vessel 1006 for subsequently receiving the target cells from the column. The remainder of the sample 1004, i.e., the portion which is not collected in the target cell collection vessel 1006, is collected in a waste receptacle 1008. Valves 1010 are provided for controlling flow from the sample 1004 to the column 1002. Valves 1012 are provided for controlling flow from the column 1002 to the target collection vessel 1006 and waste receptacle 1008. The valves 1010 and 1012 are controlled using a controller 1014.

The separation device 1002 can be any of a number of devices for selectively retaining target particles, including an immunoadsorption column. The valves 1010 and 1012 can be any of a number of devices for controlling flow and in some embodiments, are valves which operate without providing any contact with the target particles other than via sterile disposable components. The controller 1014 can be any of a number of controlling devices including mechanical controllers, pneumatic controllers, electronic controllers, optical controllers and the like. In one embodiment, the controller 1014 is an electronic controller, in one embodiment, a programmed digital processor.

In one embodiment, the apparatus depicted in FIG. 10 achieves separation in a closed sterile field manner. Closed sterile field operation is particularly important when the cell separator is to be used in connection with an invasive procedure and especially when treating a patient with high susceptibility to infection, such as an immuno-compromised patient. A number of aspects of the apparatus and the method of operation contribute to the closed sterile field characteristics. One such aspect is that the entire fluid pathway from the sample container 1004 to the target collection vessel 1006 is closed or sealed from the environment; in one embodiment, preventing exposure to any environmental component having a size greater than about 0.22 micron. As described more fully below, in one embodiment the pathway includes a series of tubing conduits, filters and vessels, all of which are connected together so as to prevent exposure to the environment. This fashion of connecting-together to prevent exposure to the environment is referred to hereinafter as "integral connection," without intending that the connection must be formed by way of integrally-formed material. Furthermore, each vessel can be configured to permit coupling to other components in order to achieve the desired separation goal and is configured to permit access, preferably aspectic access, as required, for example, for concentration or cryopreservation, purposes without substantial exposure to the environment. For example, in one embodiment, the target collection vessel 1006 is configured to permit the same vessel which is used for a collection of target particles to be also used for concentration, such as centrifugation, and/or cryo treatment, thus making it unnecessary to breach the target collection vessel 1006 for transfer purposes.

Another aspect contributing to the closed sterile field nature of the device involves providing all components which may contact the target cells as sterile, non-pyrogenic, single-use components. For example, the column 1002, as described more thoroughly below, is insertable into the apparatus in a modular fashion and is not used more than once. Similarly, the target collection vessel 1006 is used for single collection operation an is not reused with another sample. Similarly, the tubing or other conduits joining the various components are removed after a given operation of the apparatus and replaced with fresh, sterile tubing for use in separation of the next sample.

In one embodiment, the column 1002 is provided already-loaded with a substrate suspended in a stabilizing (protein-containing) buffer. In this way, it is not necessary to perform a protein-loading operation after installation of the column 1002 into the device. A separation device with a column pre-loaded with substrate in a stabilizing buffer eliminates the need for the operation or facilities to breach the closed sterile field in order to introduce or exchange buffers, consequently eliminating the attendant risk of system contamination. This configuration also simplifies the procedure, and apparatus, reducing the potential for error and resulting in a more rapid procedure.

In one embodiment of the invention, undesirable cell loss is avoided or eliminated by eliminating or reducing the number of occurrences of sharp (small radius of curvature) conduit curves or angles or providing curves having a larger radius of curvature compared to previous configurations.

In one embodiment the fluid control system includes a sensor for providing a first signal indicative of the optical density of fluid flowing out of the separation device and into the fluid collection bag. The fluid control system also includes a valve responsive to a control signal for selectively enabling the fluid flowing from the separation device to enter the fluid collection vessel. A data processor, such as a microprocessor, is provided for controlling the operation of the fluid control system. The processor is responsive to the first signal for providing the control signal to optimize the concentrations of the target cells being collected.

In one embodiment the separation device assembly includes a sample fluid supply vessel (such as a bag) for providing the sample fluid to the separation device and fluid tubing for coupling the separation device to the sample fluid supply vessel and the fluid collection vessel. The fluid control system further includes a pressure sensor coupleable to the separation device for determining the pressure of the fluid in the separation device. The pressure sensor includes a connector for coupling a pressure signal to the processor. A pump is provided and is responsive to a pump control signal for controlling the speed and direction of fluid flow in the fluid tubing. The processor is responsive to the pressure signal for providing the pump control signal to increase and decrease the pressure of the fluid in the separation device.

In one embodiment, a cell separator is provided that includes a separation device assembly for separating target cells from mixture of cells in a sample fluid. The cell separation device assembly includes a column, a sample fluid supply vessel, and a fluid collection vessel wherein the column is provided for receiving the sample fluid from the sample fluid supply vessel and for separating the target cells from the sample fluid and retaining the target cells. The fluid collection vessel is provided for subsequently receiving the target cells from the column. The cell separator includes an agitation assembly for agitating the contents of the cell separation device to assist in the release of target cells retained in the device. The agitation assembly is responsive to a drive signal for varying the amount of agitation of the contents of the separation device to vary the rate at which the target cells are released. The cell separator also includes a sensor for providing a signal indicative of the optical density of fluid flowing out of the separation device and into the fluid collection vessel. Further, the cell separator includes a valve that is responsive to a valve control signal for selectively enabling the fluid coming out of the separation device to flow into the fluid collection vessel. A processor is provided for controlling the operation of the cell separator. The processor is responsible for providing the drive signal and the valve control signal to prevent inadequate concentrations of the target cells from being collected.

DESCRIPTION OF THE PREFERRED EMBODIMENT

Figure 11:
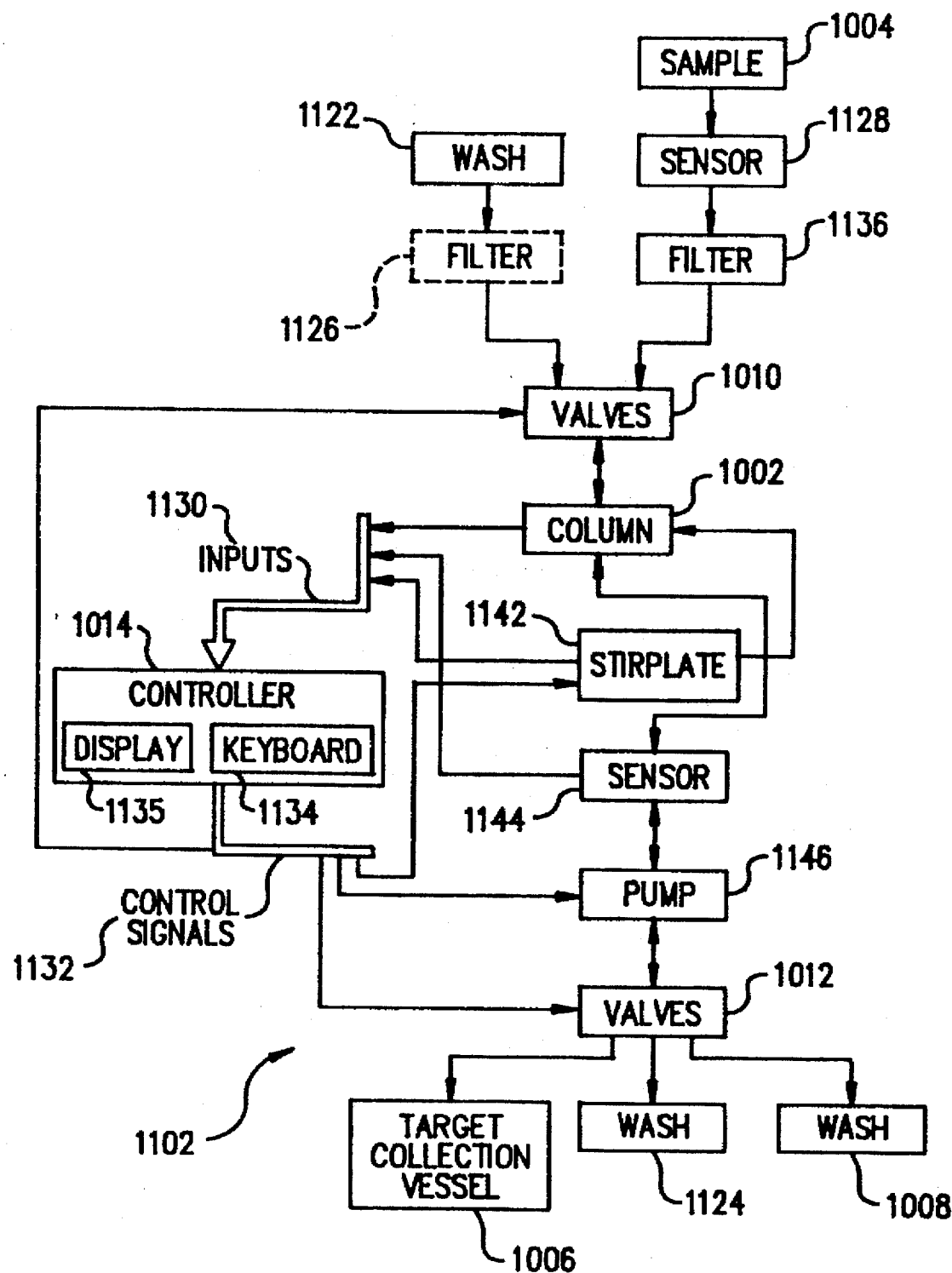
FIG. 11 is a schematic block diagram of an apparatus according to an embodiment of the present invention.

As illustrated in FIG. 11, fluid inputs to the separation device 1002 include the sample input 1004 and one or more wash fluid inputs 1122. Fluid outputs are received in the target collection vessel 1006 a used wash container 1124 and a waste vessel 1008. The wash fluid 1122 can be input, if desired, through an optional filter such as a 0.22 micron filter 1126. One example is filter number IV-3 produced by Gelman Sciences. The flow of output from the sample container 1004 is sensed by a sensor device 1128. A number of fluid sensors can be used. In one embodiment, the sensor does not contact the fluid, in order to maintain a closed preferably sterile field condition. As described below, in one embodiment, an optical density or refraction sensor is used. Information from the sensor 1128 can be used for controlling flow such as by controlling valves 1010, 1012. Preferably, the output from the sensor 1128 does not directly control the valves 1010, 1012, but instead, provides one of the inputs 1130 to the controller 1014 which, in turn, provides output control signals 1132 for controlling, among other things, the valves 1010, 1013. Employing the controller 1014, rather than directly controlling the valves 1010, 1012 with the output from the sensor 1128, provides greater flexibility and accuracy of control. For example, although a decrease in optical density of the fluid exiting the sample vessel 1004 can be used as an indication of a near-empty state of the sample vessel 1004, a decrease in optical density can also be caused by, for example, bubbles or other discontinuities in the flow. The controller 1014 can be used to distinguish between these two conditions, e.g., on the basis of duration of the change in optical density, or on the basis of the time at which the discontinuities occur (e.g., near the beginning or near the end of the predicted flow from the sample container 1004). Thus, in one embodiment, the user can input the volume of the sample using the keyboard 1134 to enable the controller 1024 to, e.g., suspend checking for flow discontinuities until most of the sample 1004 has had time to leave the container.

The flow leaving the sample 1004 can be passed through a partial filtration device for removing unwanted components such as large particles which might clog the separation device. As used herein, a filtration device is a device for at least partially excluding components larger than a given size. In one embodiment, the filtration device can be a gel. In the embodiment of FIG. 11, however, the filtration device is a filter 1136. The filter is configured to prevent passage of materials having a size greater than the effective size of the passageways in the separation device. In one example, a filter having passageways of about 0.40 micron is used. One example of such a filter is Model SQ405 produced by Pall Biomedical.

As described more fully below, one or more valves 1010 control flow from the wash 1122 and sample 1004 into the column 1002. The valves 1010 are controlled by the output control signals 1132 from the controller 1014. As described more fully below, the column 1002 is substantially sealed from the environment and has an input port and an output port coupleable to provide closed (i.e., integrally coupleable) field flow of the sample fluid into and out of the column 1002. The column 1002 includes a substrate which is configured to selectively adsorb and controllably release the target particles. In one embodiment, release of the target particles is at least partially achieved using mechanical agitation. In this embodiment, such mechanical agitation is preferably provided without the need to breach the column vessel 1002 and, in one embodiment, a magnetically-coupleable stirrer is provided in the column 1002. The stirrer can be magnetically coupled in the stirplate 1142, which is controlled by the controller 1014 as described more fully below. It is possible to provide a mechanical coupling to the column stirrer but preferably any coupling is done so as to maintain the closed field condition.

Data regarding the measured rate of agitation is provided from the stirplate 1142 as described more fully below, to the controller 1014. As described more fully below, the controller 1014 provides output signals 1132 used in setting and modifying the amount of agitation.

In one embodiment, the column vessel 1002 is pre-filled with a stabilizing buffer containing a protein such as human serum albumin (HSA). Because it is desired to avoid contamination of the target particles, the column pre-filled with substrate and stabilizing buffer, in one embodiment, is sterilized such as by electron beam irradiation (e.g., at 7.3–7.5 million electron volts for 5–10 seconds). Other means of sterilizing the pre-filled column can be used, such as steam, dry heat or gamma irradiation (see, for example, AAMI Guidelines for Sterilization of Medical Devices) where it is desired to avoid using chemical preservatives. In many cases, some period of time (e.g., 12–30 months) may elapse between the preparation of the separation device and its use for separation. It is believed irradiated protein, including irradiated human serum albumin, is stable over this period or longer.

As described below, it is also possible to provide a separation device which does not initially contain a stabilizing buffer and to load the separation device with stabilizing buffer after the column is installed in the apparatus 1102. The apparatus depicted in FIG. 11, wherein the separation device is pre-loaded with stabilizing buffer requires fewer source vessels, reduces the risk of introducing contaminants to the fluid system, enhances performance of the separation device, requires a shorter time to achieve the desired separation, and results in a device which is believed to be simpler to operate and more cost-effective.

A sensor 1144 is provided to sense or measure flow out of the separation device 1002. Output from the sensor 1144 is provided as one of the inputs 1130 to the controller 1014.

A pump 1146 is used to establish a desired direction and rate of fluid flow. Although it is possible to provide fluid flow without using a pump, such as by using gravity, a pump 1146 provides desirable control at a reasonable cost. Preferably, the pump 1146 operates while maintaining the closed, preferably sterile field condition and, in one embodiment, a peristaltic pump is used. The controller 1014 provides an output signal 1132 for establishing the direction and speed of the pump 1012.

The target collection vessel at 1006 is coupled to the remainder of the apparatus in such a way as to be able to receive the target particles while maintaining a desired closed, preferably sterile field condition.

In one embodiment, the closed, preferably sterile filed condition which has been achieved, is extended through the particle pelletizing or concentration step. In one embodiment, this is achieved by using the same vessel for both target cell collection and centrifugation. Using the same vessel has a number of advantages. It eliminates the step of transferring from one vessel to another which saves time and reduces the potential for error or introduction of contamination and also eliminates the loss of any residual particles which might resist transfer loss by adhesion to the surfaces of the vessel. Furthermore in many previous procedures, the target collection vessel was breached (such as by cutting or otherwise opening a collection bag) in order to transfer to a centrifugation vessel, thus violating or seriously degrading the closed field condition.

In order for the same vessel to be used for collection and centrifugation, the vessel must be configured to be compatible with the centrifugation process. It has been found that it is possible to perform a certain degree of cell concentration using collection vessels which are flexible plastic bags. However, centrifugation using plastic bags has not been entirely satisfactory. it has been found that, using such bags, the separated cells have a tendency to wick up the side of the bag during expression of supernatant, interfering with the desired concentration and/or resulting in loss of cells. It has also been found that, during centrifugation, cells tend to fall into wrinkles formed in the bag making them difficult to concentrate and/or retrieve. Additionally, it has been found that when centrifugation is performed using a flexible bag, there tends to be an amount of residual fluid in the bag and it has bene impossible to aspirate or otherwise remove substantially all of the fluid. Because of this, it is difficult to accurately determine the amount of residual fluid in the bag and thus it becomes difficult or impossible to calculate the proper amount of cyropreservative which should be added to the bag. Thus, although flexible collection bags provide the advantages of being relatively light, inexpensive and easily packaged and of being able to expand and contract to accommodate the fluid contained (thus eliminating or reducing the need for a vent) these aspects are believed to be for most purposes, outweighed by the lack of repeatability and safety and the difficulty in concentration or pelletizing experienced in centrifuging flexible bags. Thus, according to one aspect of the invention, the vessel which is used for both target-cell collection and centrifugation is a rigid vessel.

Figure 16:
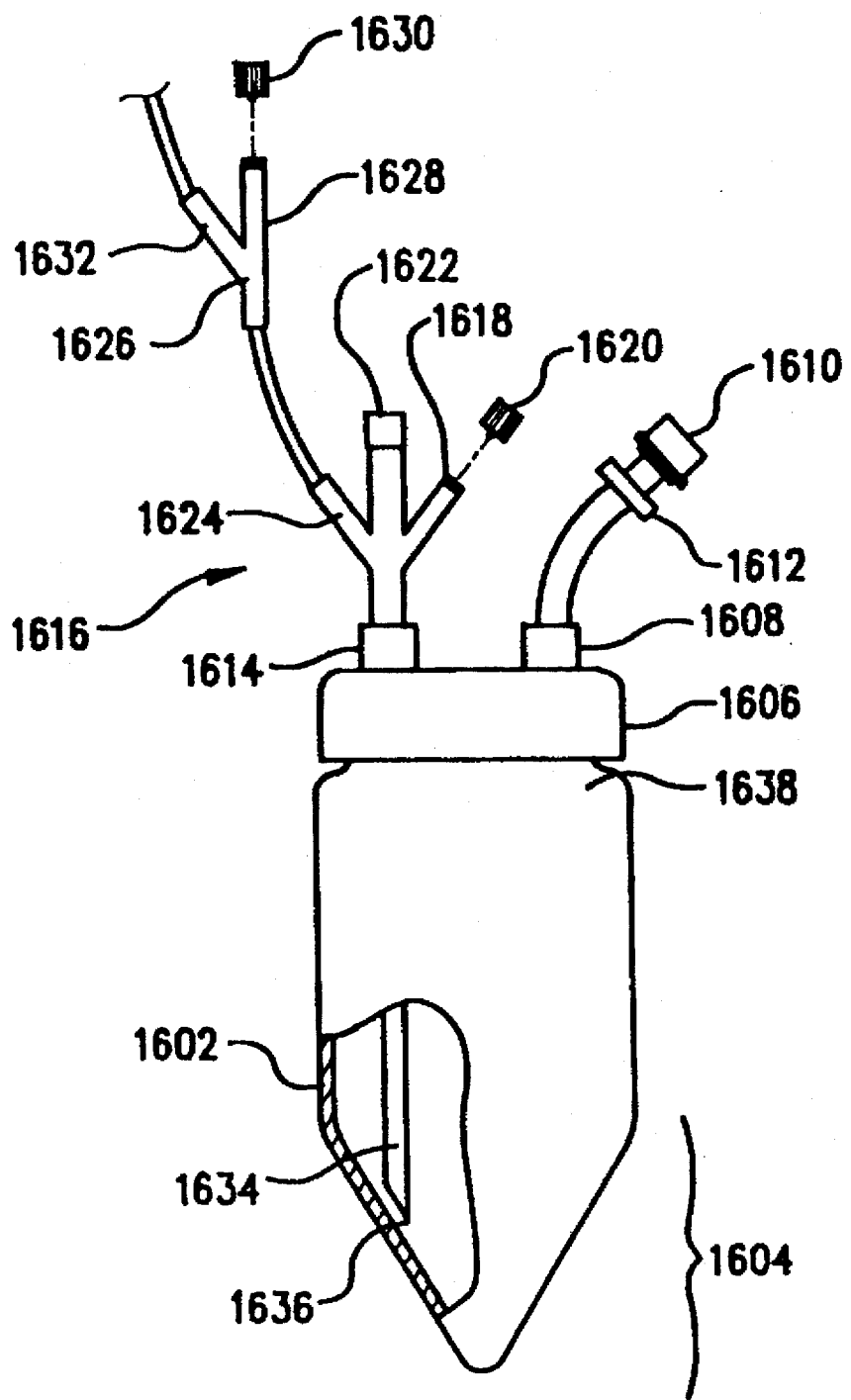
FIG. 16 is a plan view of a target collection vessel according to an embodiment of the present invention.

As depicted in FIG. 16, in one embodiment the target collection vessel is a rigid-walled tube 1602. To assist in the centrifugation process, at least a portion 1604 of the tube 16702 has a concave or tapered configuration tapering from a larger cross-sectional area to a smaller cross-sectional area. In the depicted embodiment, the tapered section generally has the shape of the frustum of a cone. The vessel 1602 is substantially sealed from the environment. In the embodiment of FIG. 16, the vessel includes a cap 1606 having at least first and second ports. A first port 1608 is connected to a filter 1610, such as a 0.22 micron filter, for venting purposes, i.e., for expelling the contents (e.g., gaseous contents) of the vessel 1602 when the vessel is being filled and for permitting entry of filtered ambient air or other gas into the vessel 1602 when fluid is withdrawn from the vessel. A valve such as a slide clamp 1612 can be provided for opening or closing the port 1608. In the depicted embodiment, a second port 1614 is coupled to a three-way connector 1616. In this embodiment one arm of the three-way connector 1618 is a secondary port sealable by a septum or other resealable filament 1620 and can be used, for example, for adding cryomedia to the vessel prior to cryotreatment. A second arm is a secondary port sealed by a septum 1622 and can be used for adding materials, such as heparin and human serum albumin, removing samples or removing separated and/or concentrated cells. The third arm 1624 can be connected to tubing for coupling to a second 2-way connector 1626. The two-way connector 1626 includes one branch 1628, which is a tertiary port sealable by septum or other resealable filament 1630, e.g., for withdrawing supernatant fluid by aspiration. The other branch 1632 can be used, for example, as a tertiary port for connection to the separation apparatus 1102 for target particle collection. In the depicted embodiment, the second port 1614 is coupled to the interior of the vessel 1602 by a conduit 1634 so that fluid which flows in and out of the port 1614 enters and exits the vessel 1602 at a location 1636 which is spaced from the location 1638 where the vent port 1608 communicates with the interior of the vessel 1602.

By providing a plurality of ports and/or connectors, the vessel 1602 can be used in a number of procedures, including collecting target particles, aspirating supernatant fluid, adding protein, removing target cells, adding cryomedia, and transferring to a storage vessel, such as a cryotube, while maintaining a substantially closed, preferably sterile field environment and without the need to perform a transfer from one vessel to another. It could be possible to perform a number of operations through a single port, such as a septum-covered port. However, reliability and confidence in freedom from contamination is enhanced by avoiding multiple reuse of a septum or similar resealable device.

The vessel 1602 can be made of a number of materials. In one embodiment, injection molded polycarbonate is used, which is believed to provide a desirably low cytotoxicity. Other materials which can be used for the vessel include polystyrene, polyacrylate, other plastics and resins, glasses, ceramics and composite materials.

Figure 17:
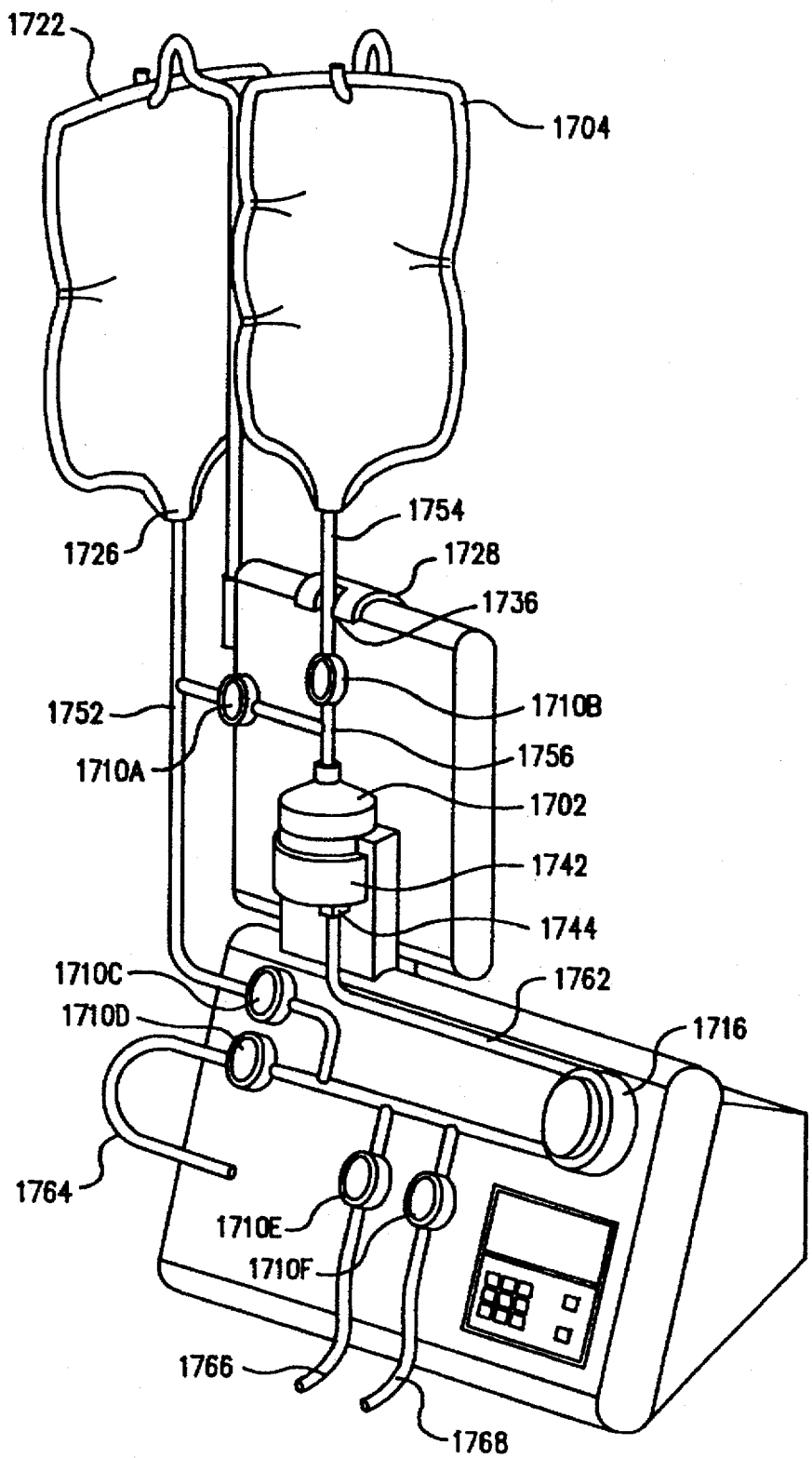
FIG. 17 is a perspective view of an apparatus according to an embodiment of the present invention.
Figure 18:
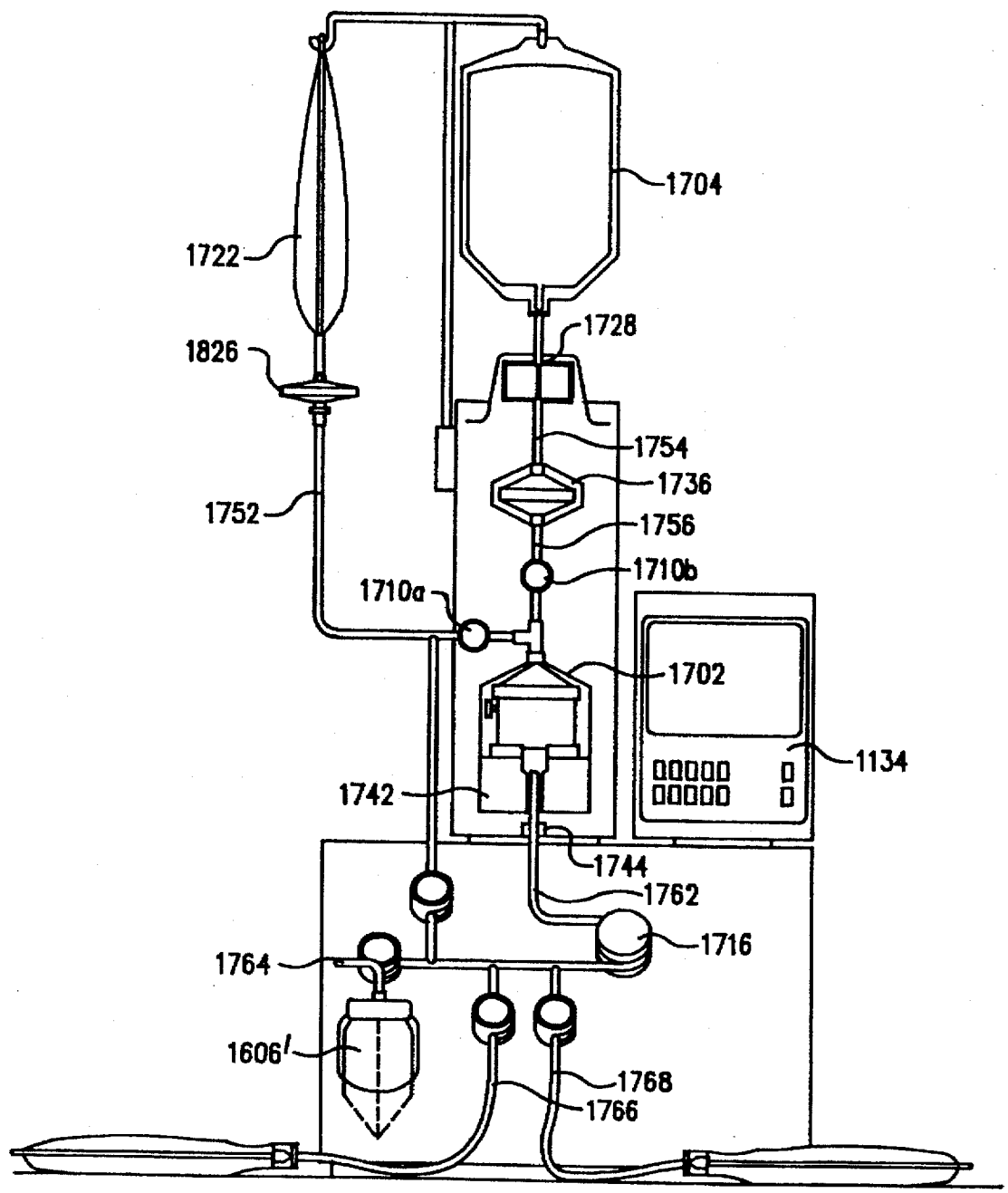
FIG. 18 is a front elevational view of an apparatus according to an embodiment of the present invention.

FIG. 17 depicts an apparatus according to one embodiment of the invention. In FIG. 17, phosphate-buffered saline (PBS) solution is provided in a flexible bag 1722 as a wash source. The solution is provided through tubing 1752 and valves 1710a to the separation device 1702. In one embodiment, depicted in FIG. 18, the solution is provided through tubing 1752 via a filter 1826. The tubing is preferably sterile flexible plastic tubing. One example is available under the trade name "Tygon." The sample, which can be, for example, human bone marrow or peripheral blood, is provided, e.g., in a flexible bag 1704 through a sensor 1728 and a filter 1736 via a valve 1710b to the column 1702 via tubing 1754, 1756. The separation device is magnetically coupled to a stirplate 1742. Outflow from the separation device 1702 passes through a sensor 1744 and, via tubing 1762, to peristaltic pump 1716. Valves 1710c, 1710d, 1710e and 1710f control flow from the wash bag 1722 to the pump 1716 and from the pump 1716 to the tubing 1764, 1766, 1768 for connection to the target collection vessel 1006, wash bag 1124 and waste bag 1008, respectively.

Figure 12:
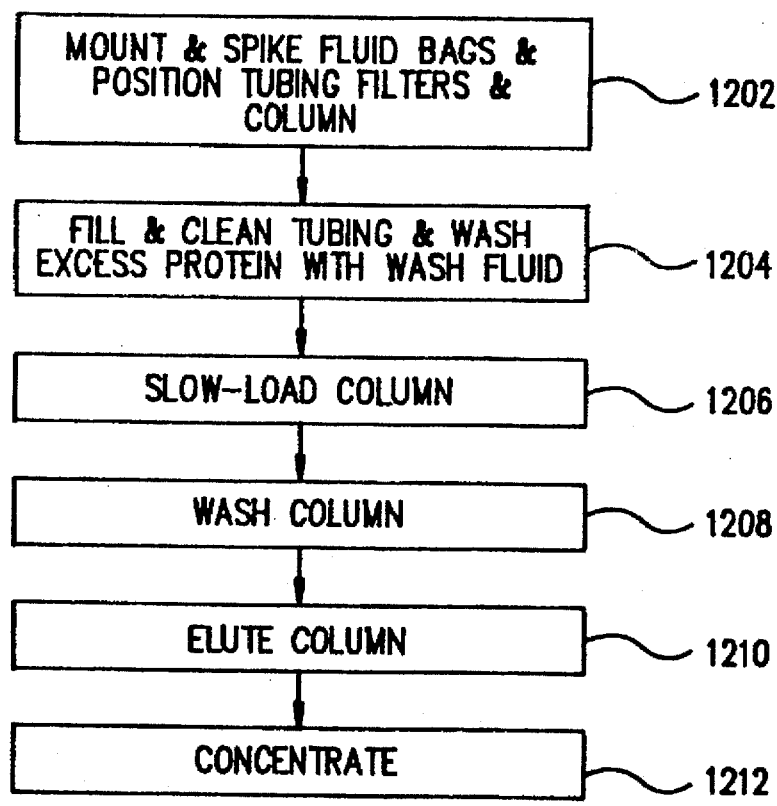
FIG. 12 is a flow diagram of a procedure according to an embodiment of the present invention.

As illustrated generally in FIG. 12, the separation procedure begins with setting up the apparatus by installing the disposable or modular components 1202. This includes installing the tubing 1752, 1754, 1756, 1762, 1764, 1766, 1768, the filters 1726, 1736 and the separation device 1702 and by mounting and spiking the bags and vessels 1722, 1704, 1006, 1124 and 1008. In the next step, e.g., under control of the controller 1014, the newly-installed tubing filters and separation device are cleaned and washed such as by flushing with wash solution to remove contaminants and wash excess protein from the protein-loaded separation device 1204. One operable washing procedure is described more fully below. After the washing procedure is finished, the column 1702 is exposed to the sample solution 1704, e.g., using a slow-load procedure, described more fully below 1206. After the column loading procedure is finished, the column is washed 1208, also under control. of the controller 1014 and eluted 1210 to recover the target particles.

Figure 13:
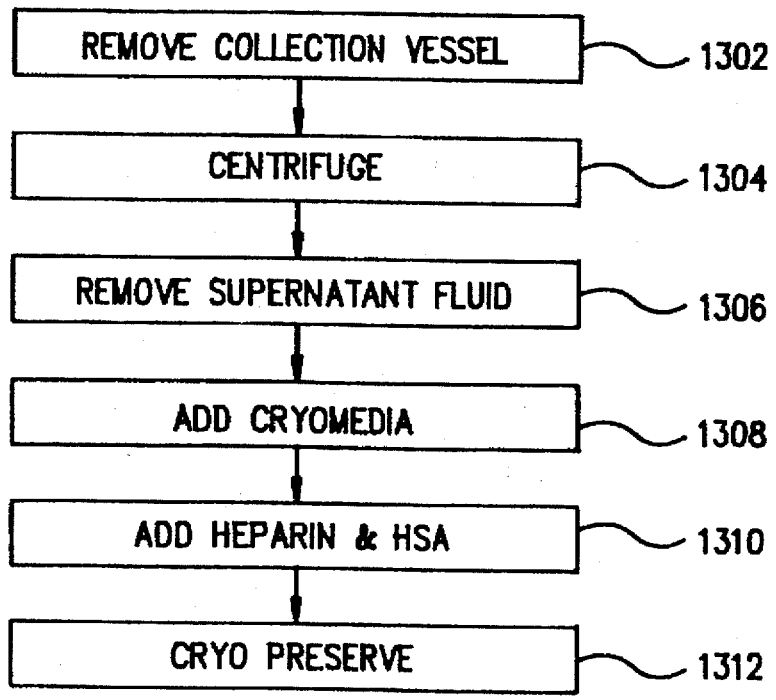
FIG. 13 is a flow diagram of a procedure according to an embodiment of the present invention.

The following procedures depend partly upon whether the apparatus has been configured to preserve closed-filed conditions beyond the separation step. If closed field conditions are to be maintained, as depicted in FIG. 13, the target collection vessel can be removed 1302 from the apparatus 1102 and the contents can be centrifuged 1304 without having to perform a vessel transfer. Next, supernatant fluid is aspirated 1306 to remove it from the vessel and cryomedia is added 1308. In some embodiments, heparin and/or human serum albumin (HSA) is added 1310. This is followed by a cryopreservation or cryotreatment step.

Figure 10:
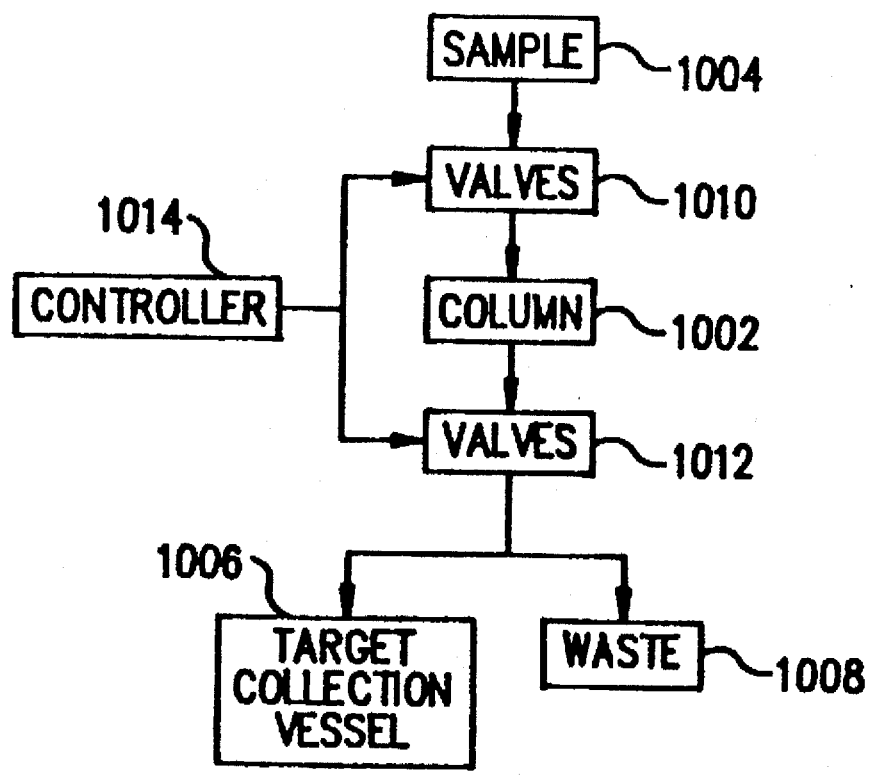
FIG. 10 is a schematic block diagram of an apparatus according to an embodiment of the present invention.
Figure 14:
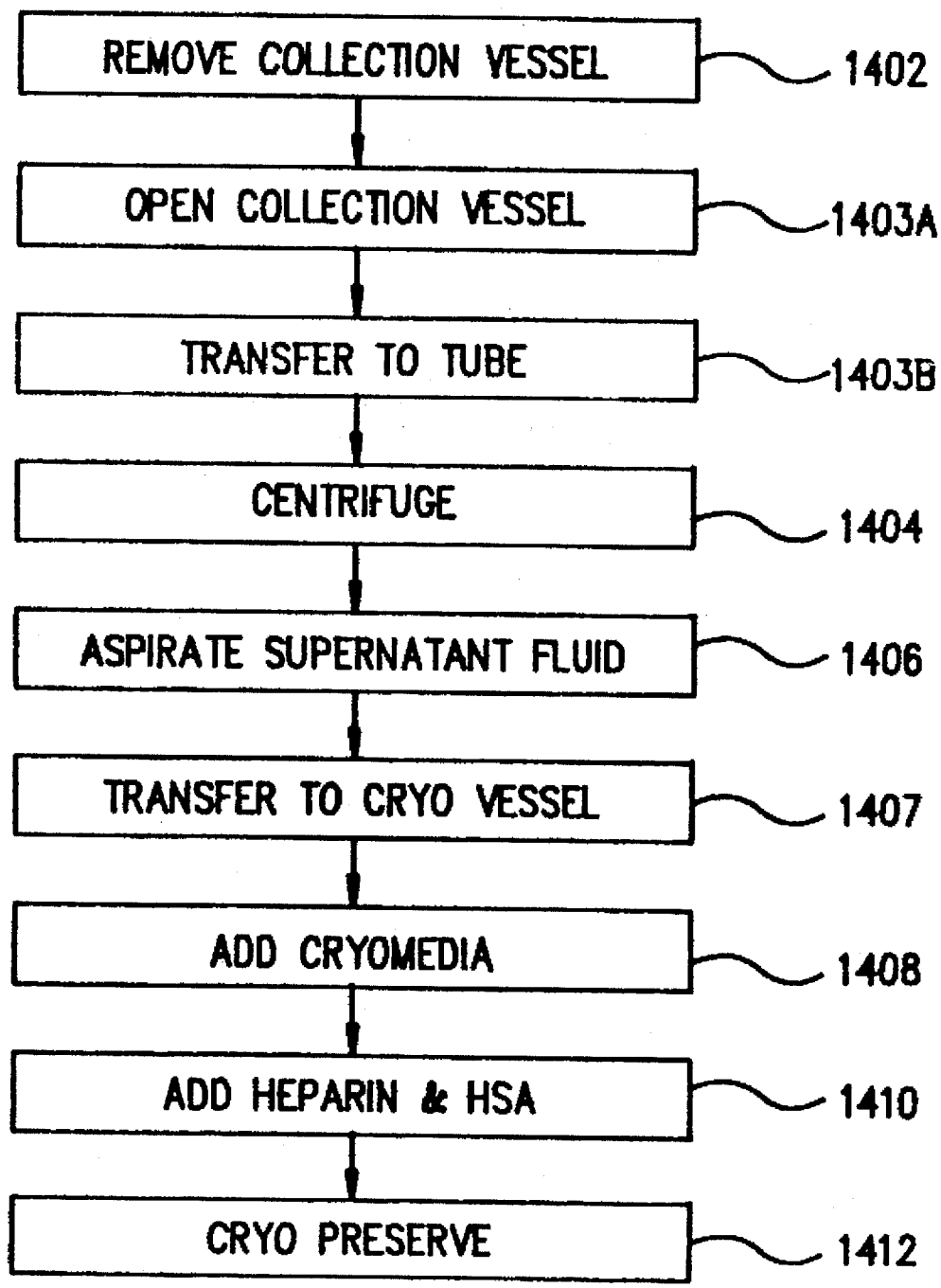
FIG. 14 is a flow diagram of a procedure according to an embodiment of the present invention.
Figure 15:
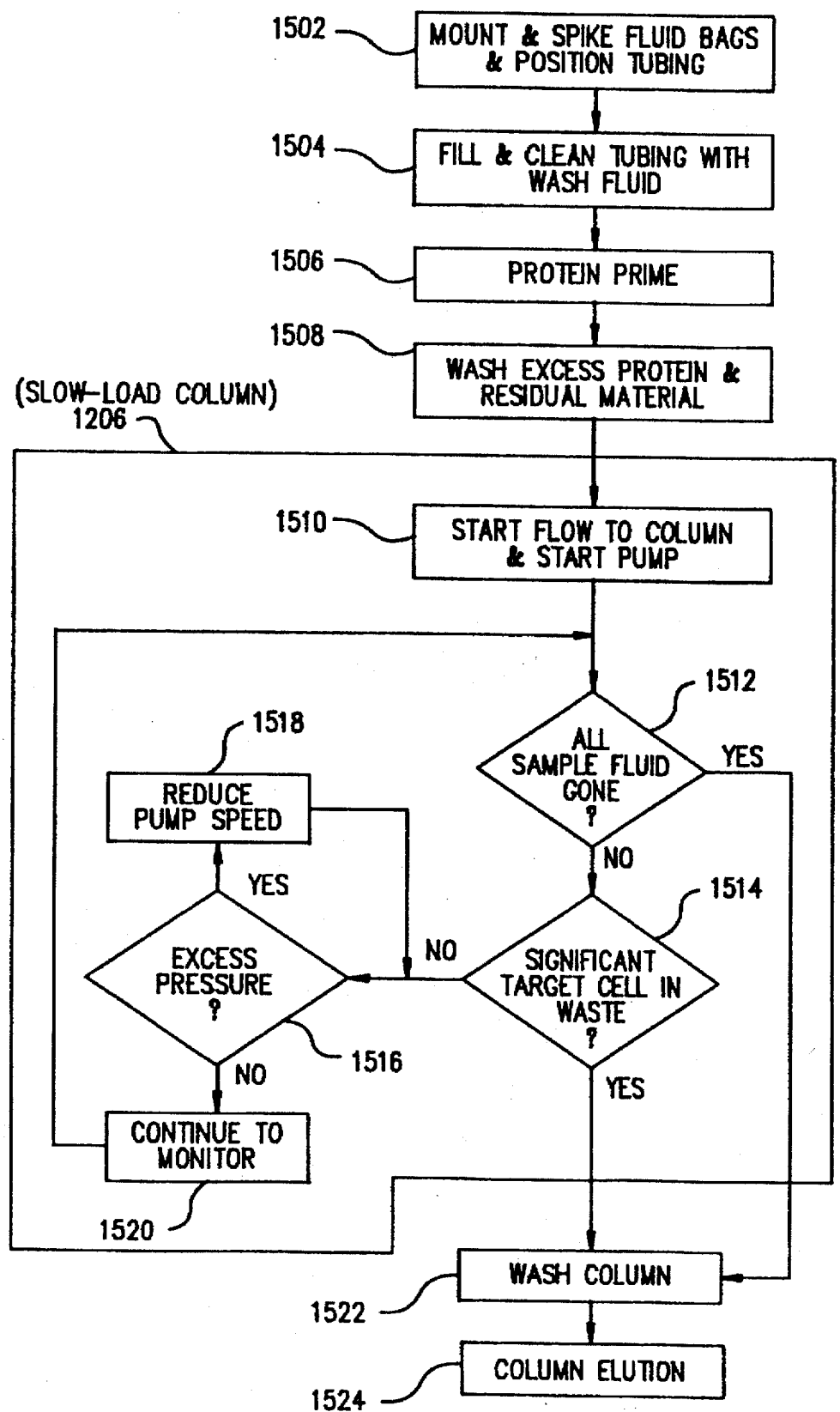
FIG. 15 is a flow diagram of a procedure according to an embodiment of the present invention.

If substantially closed field conditions are not to be preserved, another procedure, depicted in FIG. 14 can be used. The procedure FIG. 14 includes many of the steps similar to those depicted in FIG. 10, including removing the vessel 1402, centrifuging 1406, aspirating 1406, adding cryomedia 1408, adding protein 1410 and cryopreserving 1412. However, in addition, the procedure of FIG. 14 includes the steps of opening the collection vessel 1403a and transferring from the collection vessel to a centrifuge tube 1403b. The procedure of FIG. 14 also includes a step of transferring from the centrifuge tube to a cryrovessel 1407. The opening and transferring steps 1403a, 1403b, 1407, in addition to defeating or seriously compromising the closed field condition, also require additional interventional steps, additional time and increase the possibility of error.

Figure 1:
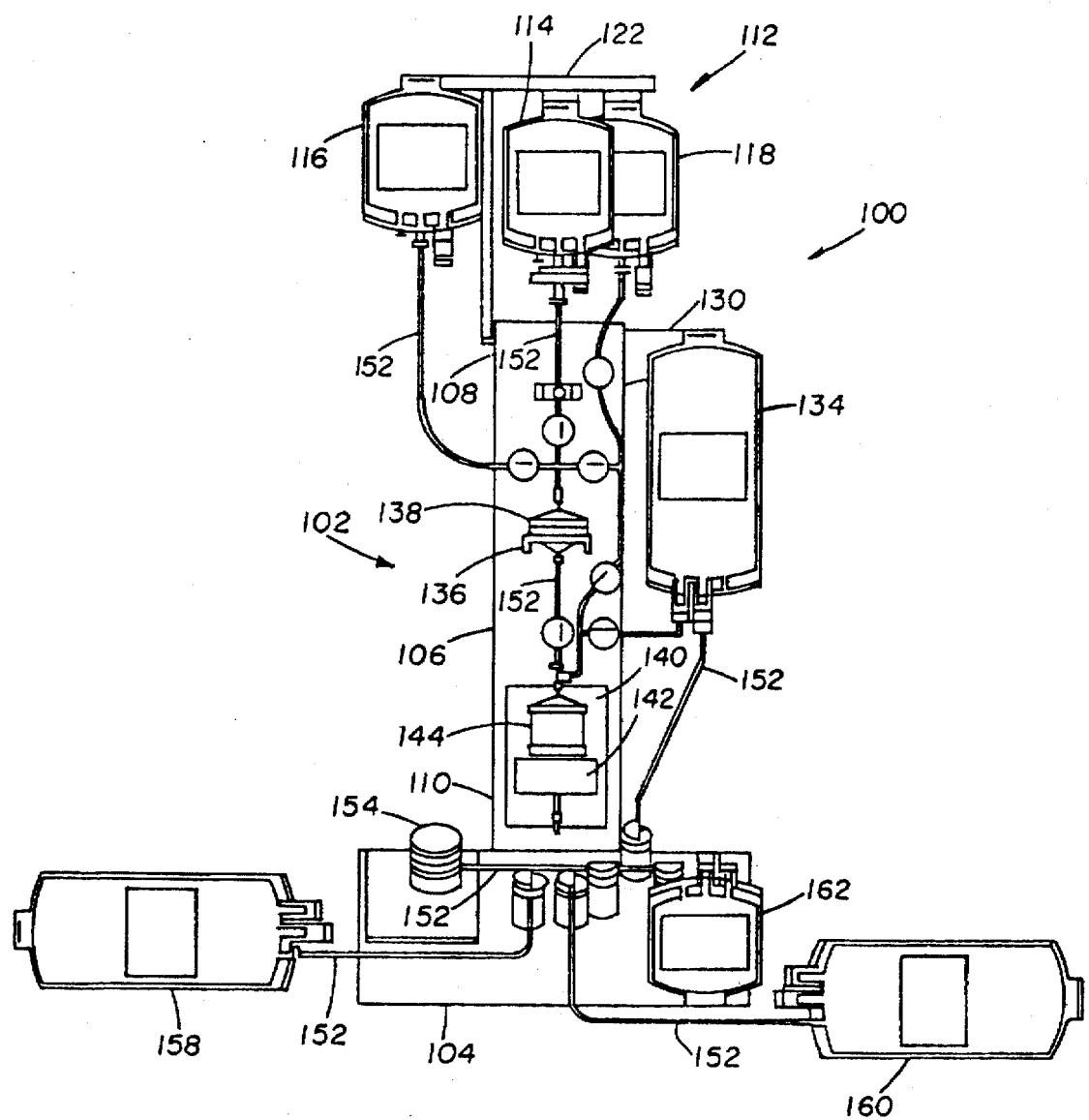
FIG. 1 is an illustrative schematic diagram of a representative cell separator device for separating target particles from a sample fluid.
Figure 2:
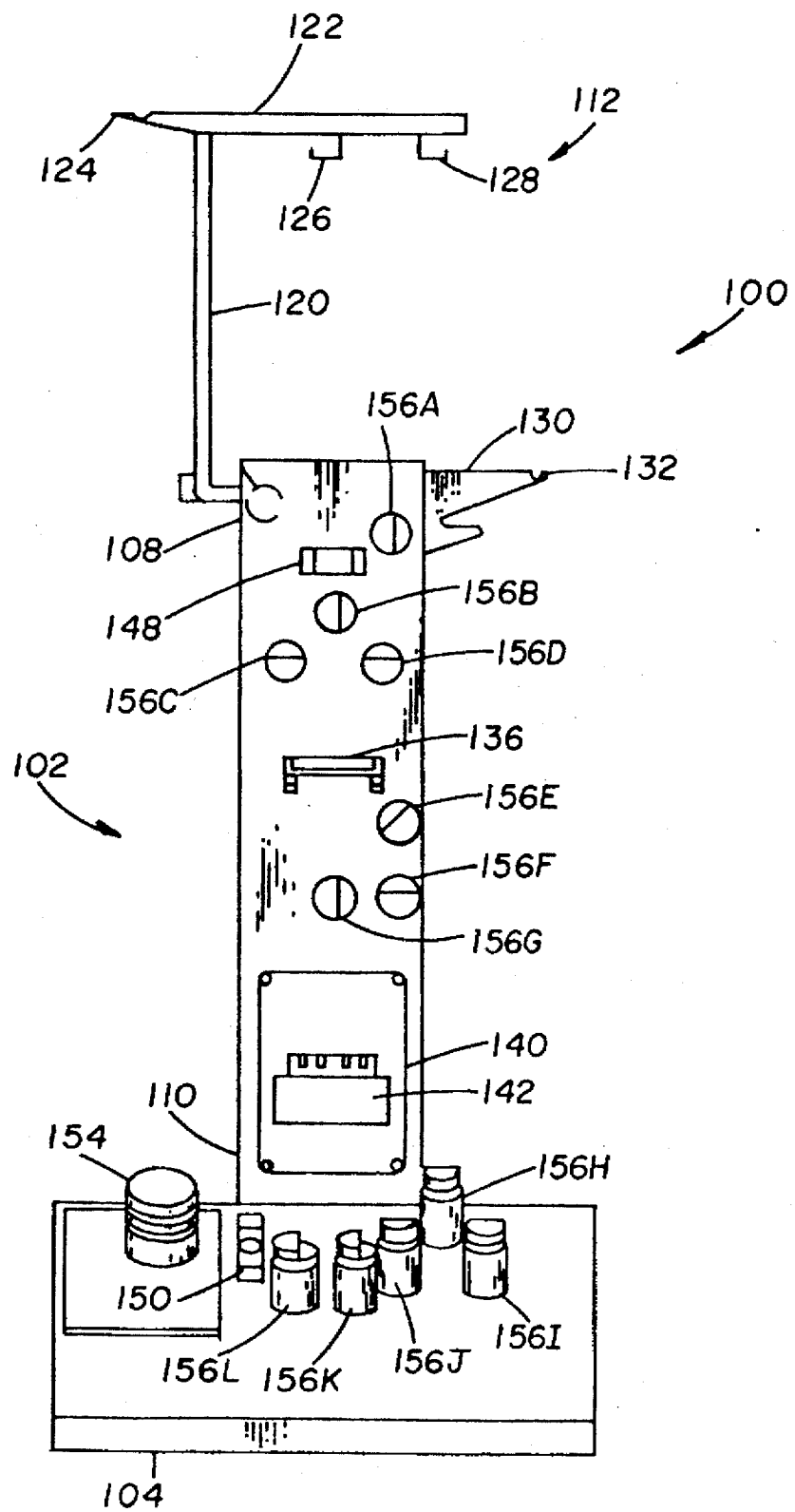
FIG. 2 is an illustrative schematic diagram of the cell separator of FIG. 1 without the removable supply and collection bag and associated tubing.

According to one embodiment, an improved cell separator 100, illustrated in FIGS. 1 and 2, is provided for separating target cells from unwanted cells. The cell separator 100 includes a frame 102 having a base 104 and a support tower 106. The support tower has a top 108 and bottom 110 wherein the bottom 110 is fixed to the base 104. The base 104 is constructed for resting on a substantially horizontal surface such that the support tower 106 extends upright from the base 104. In this construction, the base 104 provides a substantially stable foundation for supporting the support tower 106.

The cell separator 100 also includes a bag holder 112 for receiving a sample fluid supply bag 114, and first and second fluid supply bags 116 and 118, respectively. The sample fluid supply bag 114 is provided for supplying the sample fluid to the cell separator 100. Similarly, the first and second fluid supply bags 116 and 118 are provided for respectively supplying a wash solution and a protein solution to the cell separator 100, each solution for preparing the cell separator for the fluid separation, as will be discussed in more detail below.

Figure 3:
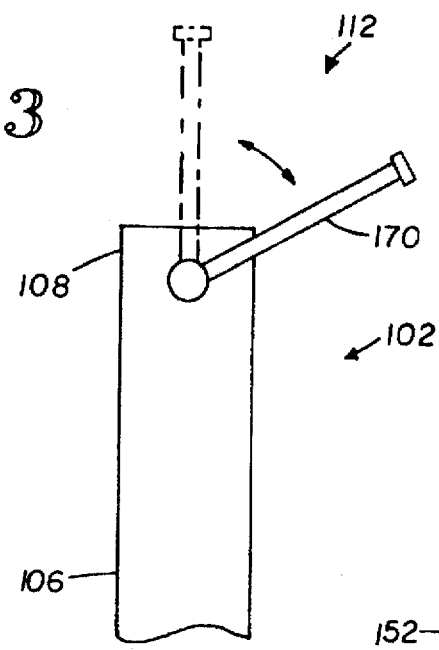
FIG. 3 is a side elevational view of a cell separator illustrating a pivotal bag holder.

The bag holder 112 includes a support rod 120, best illustrated in FIGS. 2 and 3, that is pivotally mounted to the top 108 of the support tower 106 for movement between an upright position wherein the support rod is substantially aligned with the support tower, to a pivoted position, wherein the support rod is angled with respect to the support tower (FIG. 3). The support rod is constructed for pivotal movement with respect to the support tower to enable the sample fluid supply bag 114 and the first and second fluid supply bags 116 and 118 to be easily mounted to the bag holder 112 by a user. In the pivoted position, the fluid bags 114–118 may be both mounted and spiked by a user at substantially eye level. Thereafter, the bag holder 112 is pivoted to the upright position to both move the fluid bags 114–118 out of the user's way, and to enable the user to manipulate other portions of the cell separator 100 at substantially eye level.

In one embodiment of the invention, movement of the bag holder 112 with respect to the frame 102 is accomplished by pivoting the bag holder 112 with respect to the top 108 of the support tower 106, as described above. However, other means could be provided for moving the bag holder 112 with respect to the frame 102. As an example, the support tower 106 may be constructed to pivot about first and second pivot points, thereby enabling the bag holder 112 to be lowered with respect to the base 104. As another example, the bag holder 112 may be slidably mounted upon the support tower 106, thereby enabling the bag holder 112 to be moveable with respect to the frame 102.

The bag holder 112 further includes a support beam 122 (FIGS. 1 and 2) fixed to the support rod 120 and positioned substantially transverse to the support tower 106. The support beam 122 includes a plurality of hooks 124–128 (FIG. 2) for receiving the fluid supply bags 114–118.

A fixed bag holder 130 is fixedly mounted to the top 108 of the support tower 106. The fixed bag holder 130 includes a protruding hook 132 (FIG. 2) for receiving a wash fluid source bag 134. The wash fluid source bag 134 is provided for supplying wash solution to the cell separator for cleansing the cell separator during a separation process, as will be discussed in more detail below.

A pre-column holder 136 is fixed to the support tower 106 intermediate the top 108 and bottom 110 thereof. The pre-column holder 136 is provided for receiving a pre-column 138 (FIG. 1). The pre-column 138 is provided for pre-filtering the sample fluid prior to the fluid separation to remove large particles and debris from the sample fluid. The pre-column may comprise any of a variety of commercially available devices for prefiltering the sample fluid. It will be apparent to those skilled in the art, however, that although the present invention is being described as including a pre-column 138, the pre-column 138 and pre-column holder 136 may be omitted from the cell separator 100 without departing from the invention.

One comprises a stirplate assembly 140 that is fixed to the support tower 106 intermediate the pre-column holder 136 and the bottom 110. The stirplate assembly 140 includes a column holder 142 for receiving a column 144. Generally, the column 144 is provided for separating the target particle from the sample fluid. As will be discussed in more detail below, one embodiment of the invention employs a column 144 that includes coated beads for positively selecting target cells from the sample fluid. As the sample fluid passes through the column 144, the target cells are retained within the column 144. Advantageously, the stirplate assembly 140 cooperates with the column 144 to provide controlled agitation to the contents of the column 144. Accordingly, after a sufficient quantity of the target cells have been retained within the column 144, the target cell-ligand bond may be broken by controllably agitating the contents of the column 144. Thereafter, the target cells may be eluted from the column 144 and collected as the product of the separation. The construction and operation of the stirplate assembly 140 and the column 144 will be described in more detail below.

The cell separator 100 further includes a sample sensor 148 and a column sensor 150 (FIG. 2) for sensing changes in optical density of fluid flowing in a tubing 152. The sample sensor is fixed to the top 108 of the support tower 106 for sensing changes in optical density of fluid flowing from the sample fluid supply bag 114. The column sensor 150 is fixed to the base 104 of the frame 102 for sensing changes in optical density of fluid flowing from the column 144. Each of the sample sensor 148 and column sensor 150 comprises an optical sensor 400, illustrated in FIG. 4.

Figure 4:
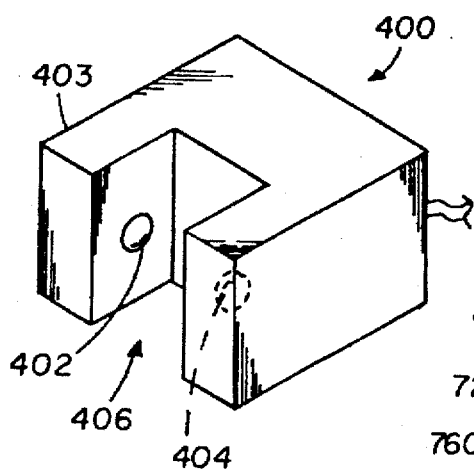
FIG. 4 is a perspective view of an optical sensor of the cell separator.

With reference to FIG. 4, the optical sensor 400 includes an optical transmitter 402 mounted in a sensor casing 403 and positioned for transmitting light to an optical receiver 404 (shown in phantom) also mounted in the sensor casing 403. The optical transmitter 402 and receiver 404 are separated by a tube channel 406 constructed for receiving the fluid tubing 152 of the cell separator 100. The optical sensor 400 is constructed for providing a sensor signal indicating the change in optical density of fluid flowing in the portion of the fluid tubing 152 positioned in the tube channel 406.

The optical sensor 400 may be readily constructed by one skilled in the art from commercially available products. In one embodiment of the invention, the optical sensor comprises an optical emitter model no. OP133 as available from the Opteck Company, and an optical sensor model no. SP100-11-11-021 as available from the Silicon Detector Company both mounted in a suitable casing. Other constructions for the optical sensor 400 will readily be apparent to those skilled in the art.

Returning to the cell separator of FIGS. 1 and 2, the sample sensor 148 is constructed for providing a sample sensor signal to indicate the change in optical density of the fluid coming out of the sample fluid supply bag 114. The column sensor 150 is constructed for providing a column sensor signal to indicate the change in optical density of the fluid flowing from the column 144. Both the sample sensor signal and the column sensor signal are provided to a data processor assembly 500 (FIG. 5) for use in controlling the operation of the cell separator 100, as will be described in more detail below.

Figure 5:
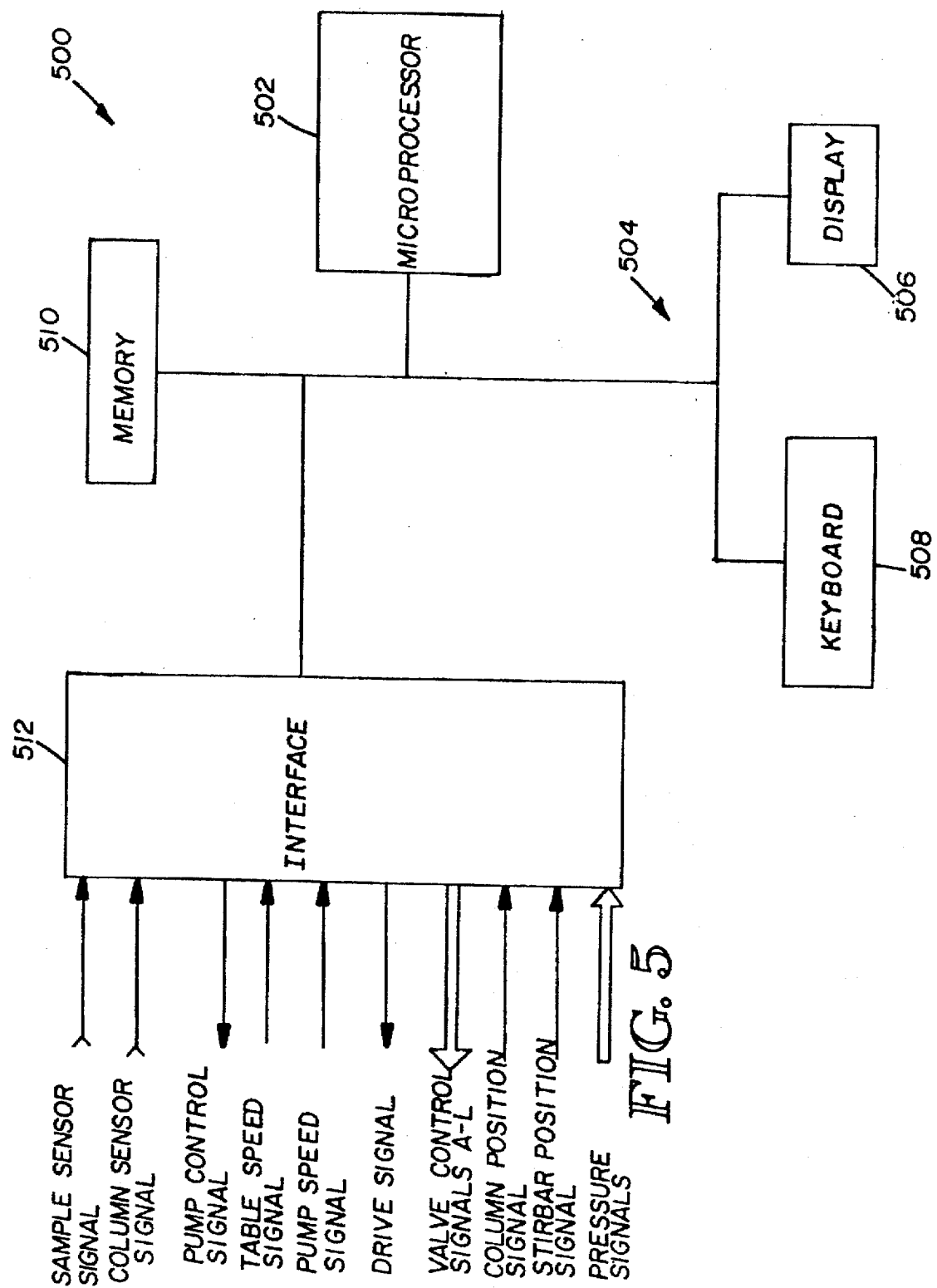
FIG. 5 is an illustrative schematic diagram of a control circuit for the cell separator.

The cell separator 100 further includes a peristaltic pump 154 for pumping fluid between the plurality of fluid bags 114–118 and 134 and the fluid tubing 152. The peristaltic pump is responsive to a pump control signal provided by the data processor assembly 500 (FIG. 5) for controlling the speed and direction of flow of fluid in the fluid tubing 152. The peristaltic pump 154 is further constructed for providing a pump speed signal to the data processor 500 (FIG. 5). The pump speed signal is indicative of the speed and direction that fluid is being pumped through the fluid tubing. An appropriate peristaltic pump for performing the above-described operation may be readily constructed by one skilled in the art. In one embodiment of the invention, the peristaltic pump comprises a Cavro 4708-5 peristaltic pump as provided by Cavro Scientific Instruments, Inc. (Sunnyvale, Calif.). It will be apparent, however, that other apparatus for providing the functions of the peristaltic pump may readily be substituted for the Cavro pump.

Figure 6:
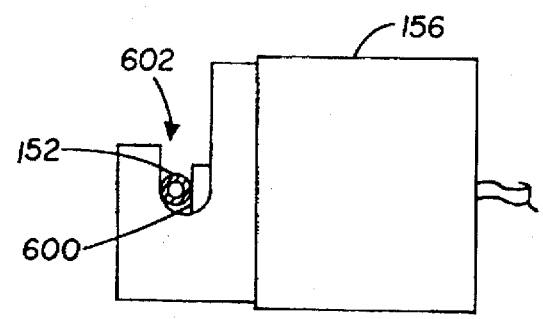
FIG. 6 is a schematic diagram illustrating the operation of a valve of the present invention.

The cell separator 100 includes a plurality of valves 156A–L (FIG. 2) for controlling the path that the fluid flows through the fluid tubing 152. Each of the valves 156 includes a solenoid (not shown) and plunger 600 (FIG. 6) separated by a valve channel 602 sized to receive the fluid tubing 152. Each valve 156 is responsive to a respective valve control signal for displacing the plunger 600 to fully or partially collapse the fluid tubing and thereby prevent or control the flow of fluid through the valve 156. The plurality of valves 156A–L are positioned to receive respective portions of the fluid tubing 152, thereby to define a plurality of fluid flow paths between the fluid bags. The data processor assembly 500 is constructed to provide the plurality of valve control signals for controlling the path that the fluid flows through the fluid tubing 152, as will be discussed in more detail below.

The cell separator 100 further includes a data processor assembly 500, illustrated in FIG. 5, that is constructed and programmed for controlling the operation of the cell separator 100. The data processor includes a microprocessor 502 for controlling the operation of the data processor assembly 500. The microprocessor 502 is coupled to a user interface 504 for providing information to and receiving information from a user of the cell separator. The user interface 504 includes a display 506 and a keyboard 508 for respectively providing information to and receiving information from a user of the cell separator. The microprocessor 502 is also coupled to memory 510 that is provided for storing programming instructions and data for controlling the operation of the microprocessor 502. The microprocessor 502 is coupled to an interface 512 for interfacing the data processor assembly 500 with the sample sensor 148, the column sensor 150, the peristaltic pump 154, the plurality of valves 156 and the stirplate assembly 140. It will be apparent to those skilled in the art that although the data processor assembly 500 is described herein by reference to microprocessor 502, user interface 504, memory 510, and interface 512, many other devices could be readily substituted therefor without departing from the true scope and spirit of the present invention. In one embodiment of the invention, data processor assembly 500 comprises a personal computer as is commercially available.

Figures 7, 7A:
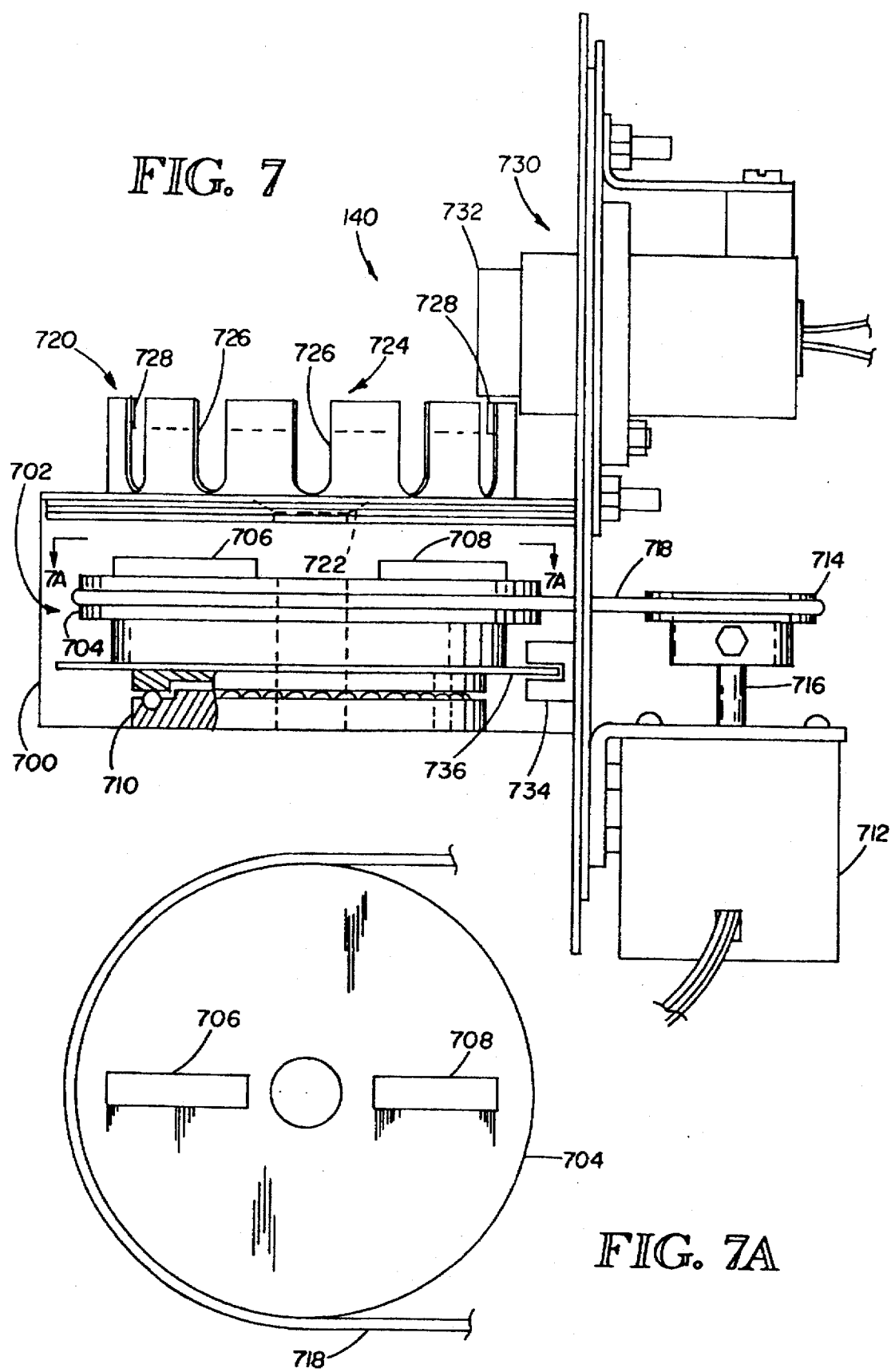
FIG. 7 is a detailed illustrative diagram of the stirplate assembly of the cell separator.
FIG. 7A is a top plan view of the magnet table of the stirplate assembly.

With reference to FIGS. 7 and 7A, the stirplate assembly 140 includes a housing 700 having mounted therein a rotating table assembly 702 for generating a moving magnetic field. More particularly, with reference to FIG. 7A, the table assembly 702 comprises a substantially flat circular magnet table 704 having mounted thereon first and second magnets 706 and 708. The magnet table 704 is mounted upon a bearing assembly 710 that rotatably supports the magnet table 704. The stirplate further includes an electric motor 712 mounted exterior to the stirplate housing 700. The electric motor 712 includes a drive wheel 714 coupled to the electric motor 712 via a shaft 716. The electric motor 712 is responsive to a drive signal received from the data processor assembly 500 for rotating the shaft 716 and drive wheel 714. In one embodiment of the invention, the electric motor 712 comprises a stepper motor responsive to a digital signal for incrementally rotating the shaft 716. It will be apparent, however, to those skilled in the art, that other motors may be readily substituted for the electric motor 712.

A drive belt 718 is coupled to the drive wheel 714 and the magnet table 704 for transferring rotational movement from the electric motor 712 to the magnet table 704. An optical encoder assembly 734 is optically coupled to an encoding wheel 736 of the magnet table 704 for providing a table speed signal indicative of the speed of rotation of the magnet table 704. The table speed signal is provided to the data processor assembly 500 to provide feedback for providing the drive signal, as will be discussed below.

By reference to FIG. 7A, those skilled in the art will appreciate that rotation of the magnet table 704 results in rotation of the magnets 706 and 708 thereby creating a moving magnetic field. It will be apparent, however, that although the stirplate assembly 140 is described herein as generating a moving magnetic field by rotating the first and second magnets 706 and 708, other apparatus, eg., electromagnetic field generating apparatus, may be provided for generating a moving magnetic field. Further, as will become apparent below, it may be desirable in some applications to create the moving magnetic field by providing other motion to the field generating magnets, eg., linear motion.

The stirplate assembly 140 also includes a positioning portion 720 mounted to the exterior of the housing 700 on the top thereat for fixedly receiving the column 144. The positioning portion is fixed to the housing 700 proximate the magnet table 704 so that the moving magnetic field is magnetically coupled to the column 144. A seat portion 722 is constructed to matably receive the column 144 (FIG. 8) to position the column proximate the magnet table 704 so that the moving magnetic field is magnetically coupled to the column 144, as will be described in more detail below. The positioning portion further includes a gripping portion 724 fixed to the seat portion 722 and constructed to engage the exterior of a column to position the column within the stirplate. The gripping portion 724 includes a plurality of extending finger portions 726 each extending upward from the seat portion 722 and ending in a contact portion 728 positioned for contacting the perimeter of the column 144.

The stirplate assembly further includes a position sensor 730 for sensing when the column is positioned in the positioning portion 720 of the stirplate assembly 140. The position sensor 730 comprises a spring actuated switch 732 positioned for engaging the periphery of the column 144 when the column is positioned within the positioning portion 720. The switch 732 is constructed to move linearly inward when the column 144 is properly positioned, to close an electrical contact and thereby provide a column position signal to the data processor assembly 500. The position sensor 730 further comprises a Hall effect sensor 800 (best illustrated in FIG. 8) that is constructed for sensing changes in the magnetic field to thereby determine the position of the first and second magnets 706 and 708 and for providing a stirbar position signal to the data processor assembly 500, indicative of the sensed change in magnetic field. In one embodiment of the invention, the data processor assembly 500 is responsive to the stirbar position signal and the table speed signal for modulating the drive signal provided to the motor 712 to thereby control the variation in the moving magnetic field. However, those skilled in the art will recognize that both sepals are not required to adequately control the speed of the magnet table 704 under many circumstances.

Figure 8:
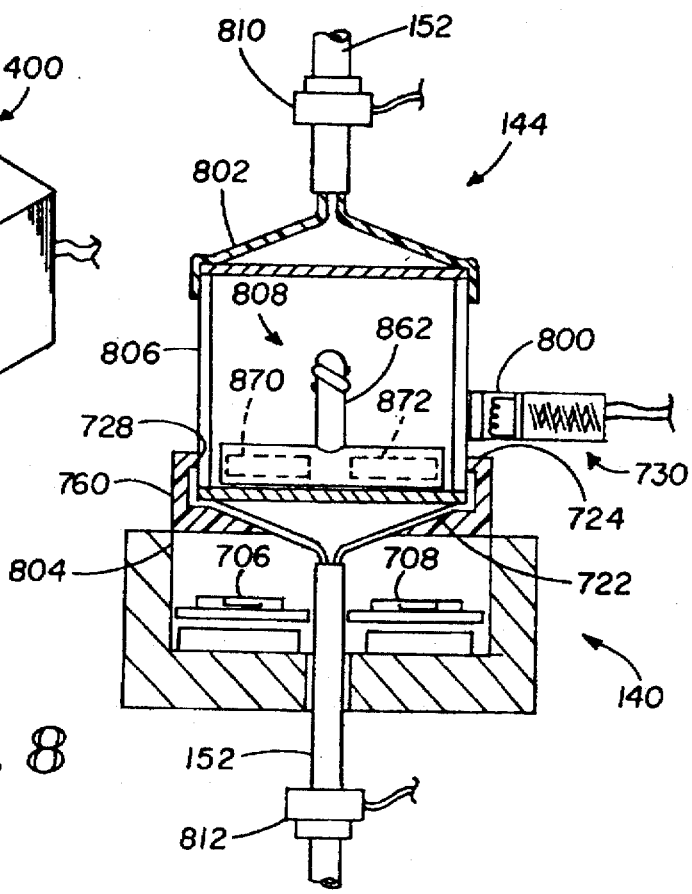
FIG. 8 is a sectional diagram of the cell separation device assembly for the cell separator.
Figure 9:
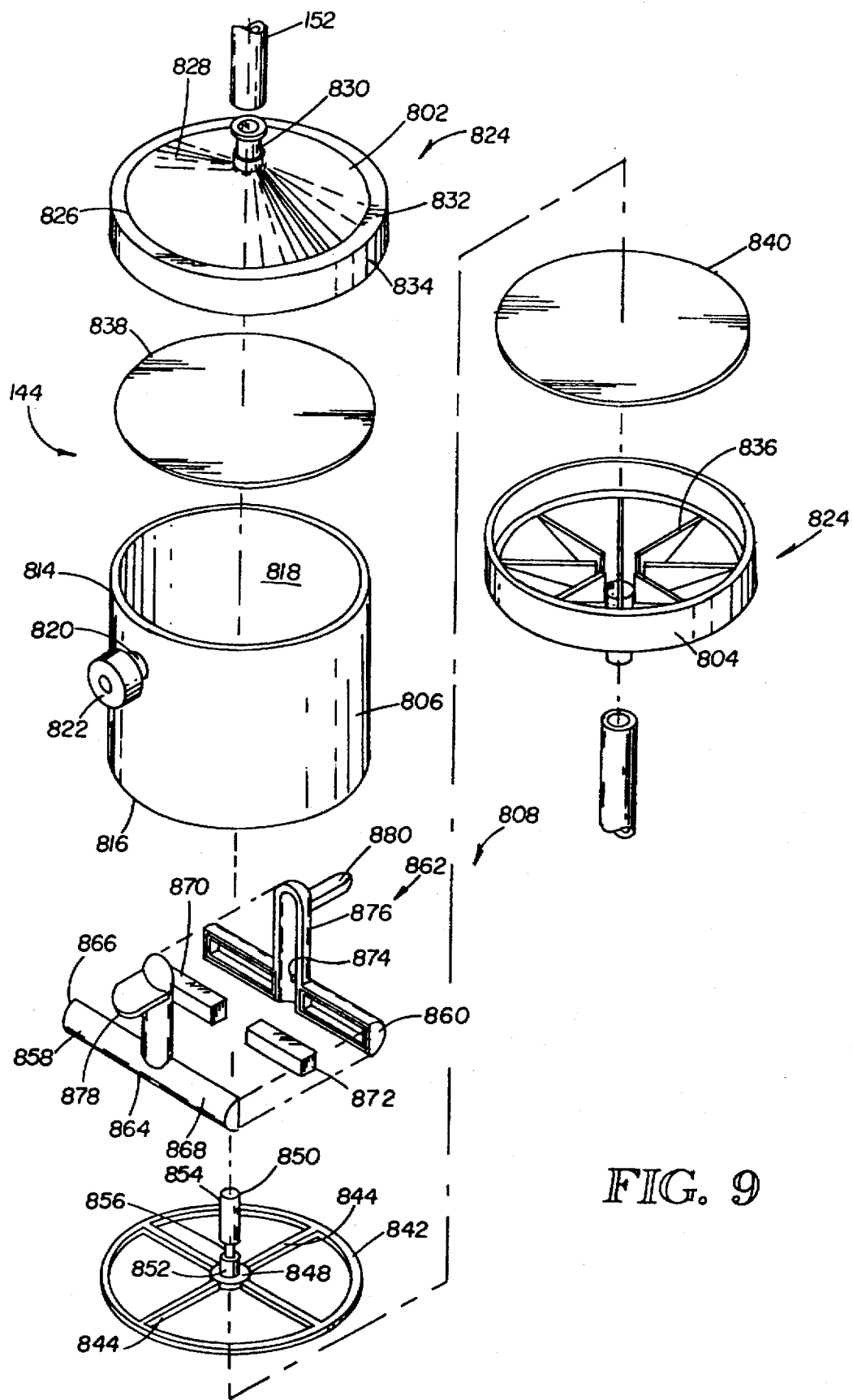
FIG. 9 is an exploded view of the separation device illustrated in FIG. 8.

With reference to FIGS. 8 and 9, a more detailed description of the construction and operation of the column 144 and stirplate assembly 140 will be provided. As mentioned above, the stirplate assembly includes a seat portion 722 and a gripping portion 720 for fixedly receiving and positioning the column 144. The column 144 includes a top 802 and a bottom 804, each separated by a cylinder 806. Further, the column includes an agitation assembly 808 that is responsive to the moving magnetic field created by the stirplate assembly 140 for agitating the contents of the column 144. In operation, the position sensor 730 determines the variation in magnetic field caused by movement of the stirplate magnets 706 and 708 so that the stirbar position signal is indicative of the speed of movement of the agitation assembly 808. The data processor assembly 500 responds to the stirbar position signal provided by the position sensor 730 to modulate the drive signal provided to the stirplate assembly 140. Accordingly, the data processor 500 is capable of precisely controlling the speed and direction of movement of the agitation assembly and, thereby, precisely controlling the agitation provided to the contents of the column 144.

Further, the tubing 152 that is coupled to the top 802 and bottom 804 of the column 144 includes first and second pressure sensors 810 and 812, respectively. The pressure sensors 810 and 812 each provide pressure signals to the data processor assembly 500. Accordingly, the data processor 500 is capable of determining the pressure differential in the column intermediate the first and second pressure sensors 810 and 812. The data processor assembly 500 responds to the determined pressure in the column 144 to control the overall operation of the cell separator 100, as will be discussed in more detail below.

With reference to FIG. 9, a more detailed description of the column 144 will be provided. The cylinder 806 includes a top portion 814, a bottom portion 816, and an inner channel 818 extending from the top portion to the bottom portion. The top and bottom portions 814 and 816 are open so that the channel 818 extends through the cylinder 806. Advantageously, the cylinder 806 includes a lock inlet 820 and a mating lock inlet cap 822 as is known in the art.

The top portion 802 and bottom portion 804 each include a rim 824 fixed to a base 826 of a hollow frustum 828 and a tube stem 830 fixed to the frustum 828 opposite the rim 824. In one embodiment, the tube stem 830 is of the type for receiving a lock cap for sealing the column prior to the coupling of the tubing 152 to the column 144. The rim 824 has a substantially circular flange 832 fixed to the base 826 and a substantially cylindrical skirt 834 fixed to the flange 832. The tube stem 830 extends outwardly from the frustum 828 and includes an inner channel for conducting liquid into and out of the top 802 and bottom 804. Each of the top and bottom further include a plurality of support ribs 836 extending radially inward from the rim 824 toward the tube stem to provide an inner frustum channel having fluid flow passageways between adjacent ones of the plurality of support ribs 836 so that fluid can flow between the base of the frustum and the inner channel of the tube stem 830. The rims 824 of the top and bottom 802 and 804, respectively, are sealed to the top and bottom portion 814 and 816 of the cylinder with the tube stems 830 extending outward from the cylinder 806.

First and second substantially planar membranes 838 and 840, respectively, each include a substantially circular perimeter to mate with the flanges 832 of the top and bottom. The first and second membranes 838 and 840 are constructed to permit the flow of particles less than a predetermined size and to prevent the flow of particles greater than the predetermined size. In one embodiment of the invention, wherein the column 144 is used for cell separation with a coated bead substrate, the membranes 838 and 840 are constructed of a size to prevent the flow of the substrate beads and thereby capture and retain the substrate within the cylinder 806.

A cylinder insert 842 is positioned intermediate the second membrane 840 and the bottom portion 816 of the cylinder. The cylinder insert 842 includes a plurality of base support ribs 844 extending across the diameter of the channel 818 and intersecting substantially at the center thereof to define a base support 848 for a shaft 850. The shaft 850 extends inward of and substantially parallel to the cylinder 806. The shaft includes a base portion 852 fixed to the base support, an extending portion 854 opposite the base portion, and a recessed portion 856 intermediate the base portion and the extending portion. The combination of the cylinder, the first and second membranes, the cylinder insert, and the top and bottom form the column 144 having a fluid flow channel defined from the tube stem 830 of the top 802 through the cylinder 806 to the tube stem 830 of the bottom 804.

The agitation assembly 808 mounted within the channel 818 of the column comprises first and second stirbar portions 858 and 860 that are constructed to be fixed together to define a stirbar 862. The stirbar 862 includes a mounting portion 864 having first and second magnet sections 866 and 868 extending radially outward therefrom. Each of the first and second magnet sections comprises a stirbar magnet 870 and 872, respectively, housed in a substantially cylindrical, nonmagnetic casing. The mounting portion 864 has a through hole of diameter larger than the diameter of the shaft 850. The mounting portion includes first and second projections 874 on opposite sides thereof extending inward of the through hole. The mounting portion is mounted to the recessed portion 856 of the shaft so that the mounting portion rotates freely about the shaft and so that the movement of the mounting portion linearly along the shaft is limited by the engagement of the first and second projections 874 with the recess portion of the shaft 850.

The stirbar 862 further includes a sleeve portion 876 having an interior chamber of diameter greater than the diameter of the extending portion 854 of the shaft 850. The sleeve portion 876 is fixed to the mounting portion 864 so that the extending portion 854 is positioned within the interior chamber and so that the sleeve portion rotates freely about the extending portion. The stirbar 862 further includes first and second propeller blades 878 and 880, respectively. The first and second propeller blades are substantially planar in configuration and are fixed to the sleeve portion 876 so that the lengths of the first and second propeller blades extend radially outward from the sleeve portion and so that the width of the first and second propeller blades is positioned at a diagonal with respect to the axis of rotation of the sleeve portion. The sleeve portion is fixed to the mounting portion so that the first and second propeller blades are substantially perpendicular to the lint and second magnet sections 866 and 868.

In operation, the first and second stirplate magnets 706 and 708 are magnetically coupled to the stirbar magnets 870 and 872 of the stirbar 862. Accordingly, rotation of the magnets 706 and 708 results in rotation of the stirbar 862. Since the speed of rotation of the magnets 706 and 708 is controlled by the data processor assembly 500, rotation of the stirbar 862 is similarly controlled by the data processor assembly 500. It will be apparent to those skilled in the art that rotation of the first and second stirbar magnets 870 and 872 will impact the change in magnetic field sensed by the Hall effect sensor 800 (FIG. 8). Advantageously, the data processor assembly 500 may be constructed to monitor the stirbar position signal provided by the Hall effect sensor 800 to determine whether the stirbar magnets 870 and 872 are magnetically coupled to the stirplate magnets 706 and 708. Essentially, this monitoring is to determine whether the change in magnetic field is as expected, given the speed of rotation of the magnetic table 704, as determined by the table speed signal.

It will be apparent to those skilled in the art that, although the present invention is described herein by reference to a stirbar 862 having first and second propeller blades 878 and 880 mounted and angled thereto, other apparatus could be provided for responding to the changing magnetic field to agitate the contents of the column 144. However, it has been determined that an extending shaft including an angled propeller blade mounted thereto, as provided in one embodiment of the invention, provides superior control over the amount of agitation to the contents of the column, than is provided by other stirbar apparatus. Further, it has been determined that the present stirbar apparatus, mounted for rotation within the column, permits control over the agitation superior to that which may be attained using stirbars that are permitted free movement within the column.

As depicted in FIG. 9, the column bottom 804 has an opening 892 communicating with a coupler 894 for connection to tubing 152'. As seen in FIG. 8, the tubing 152' passes through a hole in the center of the magnetic table 704 and thus, in the depicted embodiment, through the general region of the time-averaged magnetic field which occurs upon rotation of the magnetic table 704. Providing for passage of the tubing 152' directly downward from the column bottom 804 avoids the curving of the conduit that would be required if the conduit had to be routed around the periphery of the magnetic table 704. Avoiding such curving is helpful in avoiding the type of cell loss associated with a sharply curved or angled conduit, as discussed above. Preferably, sharp curves having a radius less than about ½", preferably less than about 1" and more preferably less than about 1 ½" are avoided in the pathway for target cells after they leave the column. This aspect of the invention is particularly important in situations in which the magnetic table magnets 706, 708 must be located relatively close to the bottom of the column 804 since a curving conduit, in this situation, would have to be sharply curved or angled, to accommodate the small height necessitated by a close proximity of the table magnets 706, 708 with the stir ban magnets 870, 872. Thus, in the embodiment depicted in FIG. 8, when the apparatus is being readied for use, a conduit, such as tubing 152' will be threaded through the hole in the magnetic table 704 and coupled to the column bottom 804.

Figure 19:
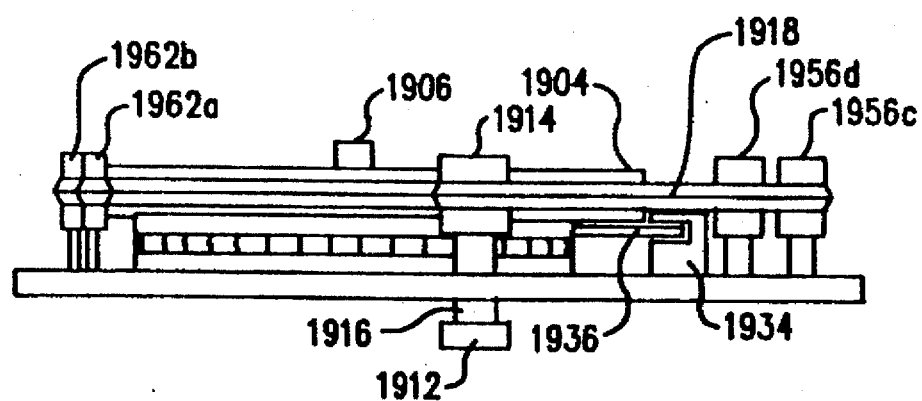
FIG. 19 is a side elevational view of a magnetic stirrer drive mechanism according to one embodiment of the present invention.
Figure 20:
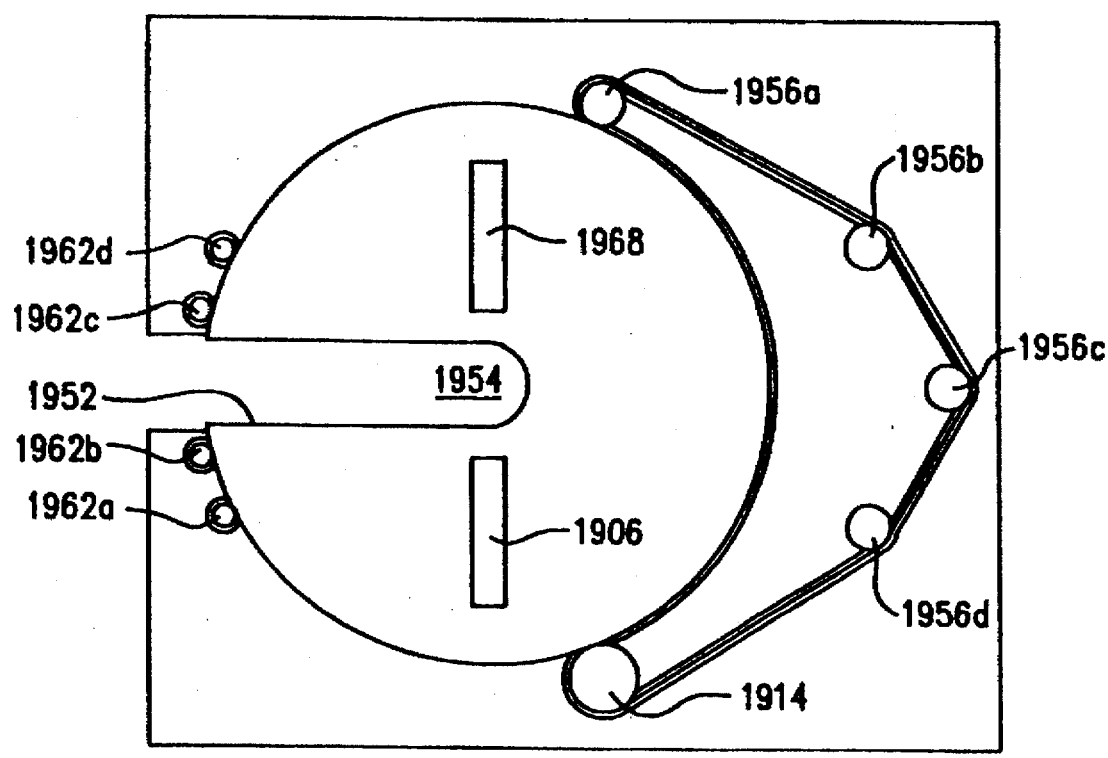
FIG. 20 is a top plan view of the drive mechanism of FIG. 19.

In another embodiment depicted in FIGS. 19 and 20, the threading of the conduit 152' through a hole is avoided by providing a magnet table 1904 that includes a slot 1952. In this way, the user, rather than have to thread the conduit 152' through a hole, can insert the conduit laterally through the slot 1952 to the desired location 1954 in the center of the magnet table 1904. Preferably, the data processor assembly 500 is configured to provide a drive signal which, responsive to a position sensor such as optical encoder 1934 and encoding wheel 1936, will assure that whenever the magnet table 1904 stopped it will be aligned substantially in the configuration depicted in FIG. 20 with the slot 1952 positioned to permit easy access by the user for insertion of the conduit 152'.

To avoid the drive belt interfering with insertion of the conduit, in the depicted embodiment 1918 is coupled to the perimeter of the magnet table 1904 along a portion of the outside edge of the drive belt 1918, so that the drive belt 1918 rests against the periphery of the magnetic table 1904 which is spaced from, and preferably, opposite to the position of the slot 1952 when the table 1904 is stopped in the preferred position depicted in FIG. 20. Thus, whereas in the configuration of FIG. 7, the belt and magnet table both move in the same rotational direction (i.e., both clockwise or both counterclockwise) in the configuration of FIG. 20, if the belt moves in a clockwise direction the table 1904 moves in a counterclockwise direction. In the embodiment depicted in FIG. 20, the belt 1918 is driven by a drive wheel 1914 connected by a shaft 1916 to a motor 1912, such an electric motor, preferably a stepper motor. The stepper motor 1912 can be controlled in a fashion similar to the control for the stepper motor 712 described above in connection with FIG. 7. The belt 1918 is held in the desired configuration by a plurality of idler wheels 1956a–1956d. In the depicted embodiment, magnet table 1904 includes a groove 1958 on its periphery for accommodating a portion of the drive belt 1918. The portion of the magnet table 1904 which is spaced from the drive belt 1918 is guided by guide wheels 1962a–1962d, preferably configured to correspond to the grooved periphery surface of the magnet table 1904. Preferably, the configuration of FIGS. 19 and 20 is substantially modularly interchangeable with the configuration of FIG. 7 and 7A. In this way, it is possible for devices having the mechanism of FIG. 7 and 7A to later be readily upgraded or retrofitted to include the configuration of FIGS. 19 and 20.

The cell separator 100 permits substantially hands-free operation by a relatively unskilled operator. Ideally, the fluid bags 114–118 and 134, along with the tubing 152 and column 144, are provided as disposable apparatus constructed for use during only a single separation process.

In operation, the user of the cell separator 100 pivots the bag holder 112 to mount the fluid bags thereon 1502 and to spike the fluid bag for operation. The bag holder 112 is then returned to the upright position and the tubing properly placed within the sensors 148 and 150 and the valves 156. Once the cell separator 100 is thus configured for operation, the user need only monitor the operation for abnormal circumstances that cannot be controlled by the data processor assembly 500.

After the user initiates the cell separation process, the data processor assembly 500 selectively opens and closes the valves 156 to permit wash fluid to flow from the wash fluid bag 134 sequentially through the valves 156H, 156J, 156G, 156E, 156C and 156A. This fluid flow acts to remove air from the tubing 152 and column 144 and to cleanse the tubing 1504 of impurities that may be in the tubing from its manufacture.

After the initial cleansing, the data processor assembly 500 controls the valves 156 to prime the tubing by allowing fluid to flow from the second fluid supply bag 118 through the valve 156A, the valve 156D, the pre-column 138, the valve 156C, the column 144, the valve 156L and into a waste bag 158. The flow of fluid in this manner primes the column and tubing with a protein solution selected to prevent substantial bonding of the target cells to the tubing. Subsequently, the microprocessor controls the valves to permit fluid to flow from the first fluid supply bag 116 through the valve 156C, the pre-column 138, the column 144, the valve 156L and into the waste bag 158. Simultaneously, fluid is permitted to flow from the wash fluid source bag 134 through the valve 156F, the column 144, and the valve 156L and into the waste bag 158. This fluid flow permits rinsing of the tubing and column to remove excess protein 1508 and to further wash residual material that may be remaining in the tubing and column from manufacture.

After the cell separator 100 has primed the tubing, it runs the cell separation process. Initially, the data processor assembly 500 opens the valves 156C and 156B to wet the tubing and filter, coupling the sample bag 114 to the tubing 152. Thereafter, the valves 156B, 156G, and 156L are controlled with the peristaltic pump to permit slow loading of the sample via the column. During this phase, the sample fluid is slowly permitted to pass through the column 1510 so that the target cells may bind with the substrate of the column 144. The unwanted material of the sample fluid is discarded in the waste bag 156. During the loading process, the data processor assembly 500 monitors the sample sensor signal and the column sensor signal to determine whether all of the sample fluid has been provided 1512 and to determine whether a significant amount of target cells are being discarded 1514 in the waste bag 156. If either of these events occur, the data processor assembly 500 will discontinue the loading step and move to another portion of the cell separation.

During the load sample step of the cell separation, the data processor assembly 500 also monitors the pressure signals provided by the pressure sensors 810 and 812 to determine whether the pressure across the column 144 is above a predetermined maximum pressure 1516. If the pressure increases beyond a maximum, the data processor assembly 500 may reduce the pressure by slowing the pump speed 1516 of the peristaltic pump 154. Other alternative steps may be taken in catastrophic cases by the user to farther alleviate excess pressure within the column 144. As an example, the user may actually reverse the flow of fluid through the column from a wash bag 160 to the wash fluid source bag 134 to aid in dislodging unwanted materials so that they may be removed from the column to decrease the overall pressure within the column.

As noted above, the data processor assembly 500 monitors 1520 the sample sensor signal provided by the sample sensor 148 to determine when the sample fluid supply is empty. Those skilled in the art will appreciate that the optical density of the fluid flowing past the sample sensor 148 will change dramatically at the instant the last portion of the sample fluid passes by the sample sensor 148. At that point, the microprocessor assembly 500 determines that no further sample fluid is available, and that the column should be emptied.

After all of the sample fluid has been passed through the column 144, the microprocessor assembly 500 will wash the column 1522 to remove non-specifically bound portions of the sample fluid. The valves 156 will be controlled to permit fluid to flow from the wash fluid source bag 134 to the waste bag 158. During this main column wash step, the microprocessor assembly 500 may be controlled to provide very light agitation to the column by providing a drive signal to the stirplate assembly 140 to slowly rotate the stirbar 862 of the column 144. However, in one embodiment of the invention, no agitation is provided during the column wash step.

After the column wash step, the target cells are eluted from the column 1524. During this step, the microprocessor assembly 500 controls the valves 156F, 156J, and 156I to permit fluid to flow from the wash fluid source bag 134 through the column 144 to a stem cell collection bag 162. During this step, the microprocessor controls the agitation provided to the column by the stirplate assembly 140 and the stirbar 162 to optimize the concentration of target cells being collected in the collection bag 162. The microprocessor assembly 500 monitors the column sensor 152 to determine the optical density of the target cells being collected, and thereby maximize concentration of the target cells. The microprocessor assembly 500 may increase the amount of target cells being collected by either increasing the amount of agitation provided to the column or by decreasing the speed at which the peristaltic pump permits target cells to be withdrawn from the column.

A number of variations and modifications of the depicted described invention can also be used. Other types of fluid movement mechanisms than a peristaltic pump can be used, including gravity feed. Other separation devices than a column can be used, including ligand-coated plates or flasks (panning) or filtration. Controlled stirrers other than magnetic stirrers can be used, including mechanically coupled stirrers, optically controlled stirrers and the like. Magnetically, coupled stirrers can be provided with a drive mechanism other than a rotating magnet table such as electronically pulsed driving mechanism and could be provided with a relatively strong magnetic driving force to permit a relatively large distance between the bottom of the column and the drive mechanism so as to permit routing a conduit around the drive mechanism while avoiding cell loss from sharply curved or angled conduits. An agitation device such as that described with the outlet flow avoiding sharply curved flow paths can be used in connection with devices other than the cell separator such as a plasma phoreisis unit. Sharp curvature of the conduit can be avoided by a device other than tubing passing through the magnetic field such as using a rotary seal mechanism. Other types of digital controllers than those described can be used including optical controllers, fuzzy logic controllers, neural network controllers and the like. Controllers other than digital processor-based controllers can be used including application specific integrated circuits, discrete logic component circuits, analog circuits and the like. Concentration and pelletization can be performed by methods other than centrifuging including precipitation sedimentation and filtration. Other types of conduit systems can be used including sterile docking devices, e.g., docking systems requiring splicing, such as the so-called "Hot knife" system available from Dupont and the "sterile connector" systems of Baxter Health Care. Although it is possible to use sterile docking systems which include splicing of conduits, it is preferable to use conduits such as the depicted tubing which can be provided in a fashion that does not require splicing by the user. Although embodiments described above include attachment of fluids systems such as a PBS bag, it is also possible to provide a system in which fluid systems such as PBS, HSA or anti-coagulant are provided pre-attached to a separation device, for example, as described in U.S. Pat. No. 5,009,654.

It is possible to use some described aspects of the invention without using others. For example, it is possible to use the closed-field aspect of the invention without using cryo-treatment. It is possible to provide the same vessel for collection and concentration without using a controller for controlling the operation of the apparatus. The apparatus can be used for separating cells other than human cells, e.g., eukaryotic cells such as plant cells and other animal cells and prokaryotic cells, such as bacteria. The apparatus can be used for separating particles, other than cells, e.g., peptides and viruses.

It will be apparent to those skilled in the art that although several embodiments of the invention have been described in detail herein, many modifications and variations may be provided without departing from the true scope and spirit of the invention. Accordingly, the invention is not limited except as by the appended claims.

What is claimed is:

1. A cell separation apparatus having a separation device assembly, the separation device assembly including a separation device for collecting target cells from a sample fluid contained in a sample container, and a fluid control system including a rigid-walled fluid collection vessel for receiving the target cells after being released from the separation device, said cell separation apparatus providing a closed sterile pathway from the sample container to the rigid-walled fluid collection vessel, comprising:

conduits coupling said separation device to said sample container and to a first port of said rigid-walled fluid collection vessel to provide a pathway along which said target cells travel from said sample container to said separation device and from said separation device to said rigid-walled fluid collection vessel in the absence of exposure to the environment, said conduits and said separation device forming a single replaceable item within said separation apparatus;

means responsive to a valve control signal for selectively enabling the fluid coming out of the separation device to flow into the rigid-walled fluid collection vessel; and means for controlling the operation of the fluid control system, by providing said valve control signal.

2. An apparatus, as claimed in claim 1, wherein said pathway is provided as a closed field sterile pathway.

3. An apparatus, as claimed in claim 1, wherein said separation device is an immunoadsorption column.

4. An apparatus, as claimed in claim 1, wherein said means for controlling comprises a microprocessor.

5. A fluid control system, as claimed in claim 1, further comprising at least a first filter coupled to at least one of said conduits, for filtering the flow through said conduit.

6. A fluid control system, as claimed in claim 5, wherein said first filter is a 0.22 micron filter.

7. A fluid control system, as claimed in claim 5, further comprising a wash solution source, coupled to said separation device wherein said first filter is located between said wash solution source and said separation device.

8. A fluid control system, as claimed in claim 1, further comprising means, between said sample container and to said separation device, for at least partial filteration of fluid which exits said sample container.

9. A fluid control system, as claimed in claim 8, wherein said means for at least partial filteration comprises a means for selectively removing particles ranging from about 5 to about 40 microns.

10. A fluid control system, as claimed in claim 8, wherein said means for at least partly cleaning comprises a pre-column containing a gel.

11. A method for providing separated, concentrated particles from a solution containing said particles, comprising:

providing said solution in a sample container, separated from the environment;

providing a separation device, coupled to said sample container by at least a first conduit, said separation device having an interior separated from the environment;

conveying at least a portion of said solution from said sample container to said interior of said separation device along said first conduit while maintaining said portion of said solution in a closed field condition in the absence of exposure of said portion of said solution to the environment;

retaining at least some of said particles in said interior of said separation device to provide target particles in said separation device;

providing a target vessel, coupled to said interior of said separation device by at least a second conduit, said target vessel having substantially rigid walls and a plurality of ports, each said port being sufficiently sealable from the environment to define a closed-field vessel, wherein at least a first of said plurality of ports of said target vessel is sealed by a filter;

conveying a plurality of said target particles from said interior of said separation device to said target vessel while maintaining said plurality of target particles in a closed sterile field condition in the absence of exposure of said plurality of target particles to the environment; and concentrating said target particles without removing said target particles from said target vessel, to maintain said plurality of target particles in a closed sterile field condition.

12. A method, as claimed in claim 11, wherein said step of concentrating comprises centrifuging said plurality of target particles.

13. A method, as claimed in claim 11, further comprising expelling at least some of the contents of said collection vessel during said step of conveying a plurality of said target particles.

14. A method, as claimed in claim 13, wherein said step of expelling comprises venting gaseous contents of said collection vessel through a filter.

15. A method, as claimed in claim 14, wherein said filter is about a 0.22 micron filter.

16. A method, as claimed in claim 13, further comprising:

cryo-treating said plurality of target particles without removing said target particles from said collection vessel, to maintain said plurality of target particles in a closed field condition.

17. The method of claim 11 wherein said separation device further comprises:

an interior of said device containing a substrate having an affinity for a target particle;

said interior of said device containing a protein substantially coating at least said substrate and interior surface of said device, prior to coupling said separation device to a particle separation apparatus.

18. The separation device of claim 17, wherein said protein comprises human serum albumen.

19. The separation device of claim 17, wherein said protein is irradiated protein.

20. A method for contamination-free, repeatable particle separation comprising:

a) providing a particle separation device having a separation column receptacle and a plurality of controllable valves;

b) providing a separation device having an affinity-specific substrate, and said separation device having an inlet port and an outlet port;

c) mounting at least first and second conduits, coupled to said inlet and outlet ports, respectively in operable proximity to said controllable valves to permit selective opening and closing of said conduits;

d) coupling said conduits to at least a sample source and a target collection vessel, said collection vessel having substantially rigid walls and a plurality of ports, each said port being sufficiently sealable from the environment to define a closed-field vessel, wherein at least a first of said plurality of ports of said collection vessel is sealed by a filter;

e) controlling said controllable valves to convey contents of said sample source to said separation device wherein at least a first plurality of target particles are retained in said separation device;

f) controlling said controllable valves to convey said first plurality of target particles to said collection vessel;

g) removing said sample source, said conduits, said separation device and said collection vessel;

h) repeating steps b) through g), using a different sample source, conduits, separation device and collection vessel to separate a second plurality of target particles in the absence of contamination by said first plurality of target particles or by the contents of a previous sample source.

21. A method, as claimed in claim 20, wherein said step of providing a separation device includes coating the interior and contents of said separation device with a protein, prior to said step of mounting said separation device.

22. A method, as claimed in claim 21, wherein said step of coating further includes irradiating said protein.

23. A method, as claimed in claim 22, wherein said irradiation comprises irradiating with an electron beam.

24. A method, as claimed in claim 20, wherein said steps of mounting and repeating are performed substantially in the absence of splicing said conduits.

* * * * *